US010793685B2

(12) United States Patent
Morita et al.

(10) Patent No.: US 10,793,685 B2
(45) Date of Patent: Oct. 6, 2020

(54) COSMETIC COMPOSITION, COSMETIC, AND EXTERNAL PREPARATION FOR SKIN

(71) Applicant: Dow Corning Toray Co., Ltd., Tokyo (JP)

(72) Inventors: Yoshitsugu Morita, Chiba (JP); Mari Wakita, Chiba (JP)

(73) Assignee: Dow Toray Co., Ltd., Tokyo (JP)

( * ) Notice: Subject to any disclaimer, the term of this patent is extended or adjusted under 35 U.S.C. 154(b) by 48 days.

(21) Appl. No.: 15/770,635

(22) PCT Filed: Oct. 28, 2016

(86) PCT No.: PCT/JP2016/082131
§ 371 (c)(1),
(2) Date: Apr. 24, 2018

(87) PCT Pub. No.: WO2017/073755
PCT Pub. Date: May 4, 2017

(65) Prior Publication Data
US 2019/0055365 A1 Feb. 21, 2019

(30) Foreign Application Priority Data
Oct. 28, 2015 (JP) ................................ 2015-212395

(51) Int. Cl.
| | | |
|---|---|---|
| *C08J 3/12* | (2006.01) | |
| *C08G 77/388* | (2006.01) | |
| *A61K 8/898* | (2006.01) | |
| *A61Q 19/08* | (2006.01) | |
| *A61K 8/25* | (2006.01) | |
| *A61Q 17/04* | (2006.01) | |
| *A61Q 5/06* | (2006.01) | |
| *A61Q 19/00* | (2006.01) | |
| *A61K 8/02* | (2006.01) | |
| *A61Q 1/02* | (2006.01) | |
| *A61Q 5/12* | (2006.01) | |
| *A61Q 15/00* | (2006.01) | |

(52) U.S. Cl.
CPC ............. *C08J 3/128* (2013.01); *A61K 8/0241* (2013.01); *A61K 8/25* (2013.01); *A61K 8/898* (2013.01); *A61Q 1/02* (2013.01); *A61Q 5/06* (2013.01); *A61Q 5/12* (2013.01); *A61Q 15/00* (2013.01); *A61Q 17/04* (2013.01); *A61Q 19/00* (2013.01); *A61Q 19/08* (2013.01); *C08G 77/388* (2013.01); *A61K 2800/412* (2013.01); *A61K 2800/524* (2013.01); *A61K 2800/612* (2013.01); *A61K 2800/623* (2013.01); *A61K 2800/651* (2013.01); *C08J 2319/00* (2013.01); *C08J 2383/04* (2013.01)

(58) Field of Classification Search
None
See application file for complete search history.

(56) References Cited

U.S. PATENT DOCUMENTS

| | | | |
|---|---|---|---|
| 5,169,561 A | 12/1992 | Gentle et al. | |
| 5,492,945 A * | 2/1996 | Morita | ...... C08J 3/124 523/212 |
| 5,756,568 A | 5/1998 | Morita et al. | |
| 5,945,471 A | 8/1999 | Morita et al. | |
| 5,948,469 A | 9/1999 | Morita et al. | |
| 2006/0058440 A1 | 3/2006 | Morita et al. | |
| 2008/0138621 A1 | 6/2008 | Morita | |
| 2011/0165246 A1 | 7/2011 | Ferber et al. | |
| 2012/0121909 A1* | 5/2012 | Kobayashi | ...... C08J 3/124 428/404 |
| 2015/0189867 A1 | 7/2015 | Kroupa et al. | |

FOREIGN PATENT DOCUMENTS

| | | |
|---|---|---|
| CN | 102083309 A | 6/2011 |
| CN | 104472530 A | 4/2015 |
| EP | 0393511 A2 | 10/1990 |
| EP | 2325261 A1 | 5/2011 |
| EP | 2556818 A1 | 2/2013 |
| EP | 2796509 A1 | 10/2014 |
| JP | H04348143 A | 12/1992 |
| JP | H07102075 A | 4/1995 |
| JP | H09208709 A | 8/1997 |
| JP | 2006188592 A | 7/2006 |
| JP | 2007176822 A | 7/2007 |
| JP | 2011026469 A | 2/2011 |

(Continued)

OTHER PUBLICATIONS

Database WPI Week 198735 Thomson Scientific, London, GB; AN 1987-247981; XP002789928, & JP S62 171913 A (Toray Silicone Co., Ltd.), Jul. 28, 1987 (Jul. 28, 1987)*abstract*.
Database WPI Week 201468 Thomson Scientific, London, GB; AN 2014-S67443; XP002789753, & CN 103 937 258 A (Univ Shandong), Jul. 23, 2014 (Jul. 23, 2014) *abstract*, *example 4*.
PCT/JP2016/082131 International Search Report dated Jan. 24, 2017, 2 pages.
English language abstract and machine translation for JP2007176822 (A) extracted from http://worldwide.espacenet.com database dated May 17, 2018, 29 pages.

(Continued)

*Primary Examiner* — Marc S Zimmer
(74) *Attorney, Agent, or Firm* — Warner Norcross + Judd LLP

(57) ABSTRACT

A composite silicone rubber particle is disclosed, wherein a part or entire surface of the silicone rubber particle is covered by a fine particle, a surface of which is modified by a functional group containing quaternary ammonium salt. Manufacturing methods of the composite silicone rubber particle are also disclosed, as well as a cosmetic product composition containing the composite silicone rubber particle. The composite silicone rubber particle has hydrophilicity and dispersibility while maintaining excellent fluidity, contains no harmful methanol, and has antimicrobial activity.

20 Claims, No Drawings

(56) References Cited

FOREIGN PATENT DOCUMENTS

| JP | 2015520291 A | 7/2015 |
|----|--------------|--------|
| WO | WO2004055099 A1 | 7/2004 |
| WO | WO2006073055 A1 | 7/2006 |
| WO | 2016100830 A1 | 6/2016 |

OTHER PUBLICATIONS

Machine assisted English translation of CN104472530A obtained from https://patents.google.com/patent dated Apr. 28, 2020, 7 pages.

* cited by examiner

COSMETIC COMPOSITION, COSMETIC, AND EXTERNAL PREPARATION FOR SKIN

CROSS-REFERENCE TO RELATED APPLICATIONS

This application is the National Stage of International Application No. PCT/JP2016/082131 filed on 28 Oct. 2016, which claims priority to and all advantages of JP Patent Application No. 2015-212395 filed on 28 Oct. 2015, the content of which is hereby incorporated by reference.

TECHNICAL FIELD

The present invention relates to a cosmetic composition and a cosmetic and an external preparation for skin containing the same.

BACKGROUND ART

A silicone rubber particle is used as an additive for cosmetic products, paints, inks, thermosetting organic resins, thermoplastic organic resins, and the like, and, in particular, is suitably used as internal stress relaxation agents for thermosetting organic resins, surface lubricants for organic resin films, and tactile sensation enhancing agents for cosmetic product compositions. However, such a silicone rubber particle tends to aggregate easily and therefore has poor fluidity as well as poor dispersibility into aqueous compositions such as water-based paints and cosmetic products. Therefore, if a cured silicone particle is not dispersed uniformly into an aqueous composition and is present in the aqueous composition in an aggregated state, there are problems: a uniform matte effect was not sufficiently provided by the cured silicone particle in the case of a water-based paint, and the appearance or tactile sensation was poor in the case of a cosmetic product.

A composite silicone rubber particle wherein the fluidity is improved by covering the surface of the silicone rubber particle with an inorganic fine particle have been proposed (see Japanese Unexamined Patent Application Publication No. H4-348143, Japanese Unexamined Patent Application Publication No. H7-102075, Japanese Unexamined Patent Application Publication No. H9-208709, and Japanese Unexamined Patent Application Publication No. 2007-176822). However, such a composite silicone rubber particle exhibits poor hydrophilicity, which leads to a problem of poor affinity toward aqueous composition when the particle is blended into an aqueous composition. In addition, there is a problem of tactile sensation of a hard inorganic particle when such a particle is blended into a cosmetic product composition.

A composite silicone rubber particle with enhanced hydrophilicity by adhering surfactant an inorganic fine particle and the composite silicone rubber particle and a composite silicone rubber particle enhanced hydrophilicity by adhering polyhydric alcohol to an inorganic fine particle have also been introduced (International Patent No. WO/2004/055099 and Japanese Unexamined Patent Application Publication No. 2011-026469). However, there are problems of limited composition designs for cosmetic products using such a composite silicone rubber particle, because it is necessary to adhere a large amount of surfactant or polyhydric alcohol in order to maintain sufficient hydrophilicity.

A composite silicone rubber particle in which the surface of the silicone rubber particle covered by an inorganic fine particle is treated with an organic silicon compound or a (partial) hydrolysate thereof in order to reduce aggregability have been proposed (Japanese Unexamined Patent Application Publication No. 2006-188592). However, no organic silicone compound having an ammonium base-containing organic group in an organic silicon compound has been taught or suggested. Besides, the composite silicone rubber particle covered with an organosilicon compound has a problem that the composite silicone rubber particle contains silicon-bonded methoxy group or methanol and is therefore difficult to blend in a cosmetic product composition. Further, the notion of adding an organic group containing a polar ammonium salt functional group to the silicone rubber particle was not considered because aggregation has been an issue in the first place.

With regard to an antimicrobial silicone rubber particle, it has been proposed that a silver-supporting silicone rubber particle supporting a silver-containing particle has antimicrobial effect (Japanese Unexamined Patent Application Publication (Translation of PCT Application) No. 2015-520291). In a mixing step for the silver-containing particle and the silicone rubber particle, which is a dry manufacturing method of supporting the silver-containing particle on the silicone rubber particle surface, container contamination or poor usage efficiency of the silver material is an issue, due to the adherence of the silver compound to the inside of the mixing container. In a wet method, the yield of supporting the silver material on the surface of the silicone rubber is low due to factors such as silver ion deposition, the reduction of silver ions on the silicone rubber particle surface, and the removal of solvents such as water. Furthermore, it has been known that the particle size and the number of particles of the silver-containing particle have a substantial effect on antimicrobial action; so in order to enhance the antimicrobial activity, the compounded amount of the silver compound needed to increase, which leads to high manufacturing cost, resulting in a problem of limited range of usage.

CITATION LIST

Patent Literature

Patent Document 1: Japanese Unexamined Patent Application Publication No. H04-348143A
Patent Document 2: Japanese Unexamined Patent Application Publication No. H7-102075A
Patent Document 3: Japanese Unexamined Patent Application Publication No. H9-208709A
Patent Document 4: Japanese Unexamined Patent Application Publication No. 2007-176822
Patent Document 5: WO/2004/055099
Patent Document 6: Japanese Unexamined Patent Application Publication No. 2011-026469A
Patent Document 7: Japanese Unexamined Patent Application Publication No. 2006-188592A
Patent Document 8: Japanese Unexamined Patent Application Publication No. 2015-520291A

SUMMARY OF INVENTION

Technical Problem

One object of the present invention is to provide a composite silicone rubber particle which has hydrophilicity and dispersibility while maintaining excellent fluidity and is capable of exhibiting functionality such as antimicrobial activity or hair adhesion. Another object of the present invention is to provide a composite silicone rubber particle with extremely low the methanol content. Another object of the present invention is to provide a composite silicone rubber particle with an improved tactile sensation, a manufacturing method of efficiently producing the particle, a uniform dispersion of the particle, and a cosmetic product composition comprising the particle.

Solution to Problem

Composite silicone rubber particle of the present invention is characterized in that a part or entire surface of the silicone rubber particle is covered by a fine particle, the surface of which is modified by a functional group containing quaternary ammonium salt.

The manufacturing method of a composite silicone rubber particle of the present invention has at least the following steps:

step 1: forming a composite silicone rubber particle by mixing a fine particle and a silicone rubber particle using a mechanical force; and step 2: modifying surface of the fine particle of the composite silicone rubber particle obtained in step 1 with a silicon compound having a functional group containing quaternary ammonium salt and being capable of forming a chemical bond on the surface of the fine particle.

The dispersion of the present invention is a uniform mixture of the composite silicone rubber particle of the present invention and a liquid compound.

The cosmetic product composition of the present invention contains the composite silicone rubber particle of the present invention.

Advantageous Effects of Invention

Composite silicone rubber particle of the present invention is characterized in that the composite silicone rubber particle has hydrophilicity and dispersibility while maintaining excellent fluidity, has antimicrobial activity and hair adhesion, and does not contain methanol.

The manufacturing method of the present invention is characterized in that a composite silicone rubber particle which has antimicrobial activity and hair adhesion and does not contain methanol can be produced efficiently. The dispersion of the present invention is characterized in that a composite silicone rubber particle is dispersed uniformly and in that the dispersion has antimicrobial activity and hair adhesion and does not contain methanol. The cosmetic product composition of the present invention has a good feel of use while having antimicrobial activity and hair adhesion and not containing methanol.

DESCRIPTION OF EMBODIMENTS

The composite silicone rubber particle of the present invention is characterized in that a part or entire surface of the silicone rubber particle is covered by a fine particle, the surface of which is modified by a functional group containing quaternary ammonium salt.

The functional group containing quaternary ammonium salt of the composite silicone rubber particle of the present invention has a hydrocarbon group and is straight-chain (including substantially straight-chain). "Substantially straight-chain" refers to a chain, which includes branched chains in some groups but such a branched chain does not affect the structure of the quaternary ammonium salt or the properties of the functional group itself. The composite silicone rubber particle of the present invention may have a functional group containing one or more quaternary ammonium salts.

The average particle size of the silicone rubber particles is preferably in the range of from 0.1 to 500 um, more preferably in the range of from 0.1 to 200 um, even more preferably in the range of from 0.1 to 100 um, and particularly preferably in the range of from 0.1 to 50 um. This is because silicone rubber particle having an average particle size of less than the lower limit of the range described above is difficult to prepare, and the surface thereof is difficult to cover with a fine particle, whereas when the average particle size exceeds the upper limit of the range described above, the dispersibility of the resulting composite silicone rubber particle in a solvent, a paint, or a cosmetic is diminished.

The average particle size of the silicone rubber particles can be measured with a commercially available laser diffraction-type particle size distribution analyzer (for example, LA-750 produced by Horiba, Ltd.) for a water dispersion or ethanol dispersion of the silicone rubber particle, for example, and may be determined in terms of the median diameter thereof (particle size corresponding to 50% of the cumulative distribution; 50% particle size). The shape of the silicone rubber particle is not particularly limited but is preferably spherical or substantially spherical from the perspective of ensuring excellent dispersibility in paints or cosmetics and enabling a dramatic improvement in matte of paints or feel of use of cosmetics.

The type A durometer hardness of the silicone rubber particle defined in JIS K6253 is preferably from 10 to 90, more preferably in the range of from 15 to 80, and particularly preferably in the range of from 20 to 70. This is because when the type A durometer hardness is less than the lower limit of the range described above, the fluidity of the resulting composite silicone rubber particle is diminished, and it becomes difficult to form a coating having a good matte when the particle is blended into a coating, whereas when the type A durometer hardness exceeds the upper limit of the range described above, it becomes difficult to enhance the feel of use of the cosmetic. The type A durometer hardness can be determined by curing a silicone rubber composition to form the silicone rubber particle into a sheet shape and measuring the hardness of the rubber sheet.

Examples of the silicone rubber composition to form the silicone rubber particle include addition reaction-curable silicone rubber compositions comprising at least organopolysiloxanes having at least two alkenyl groups per molecule, organopolysiloxanes having at least two silicon-bonded hydrogen atoms per molecule, and platinum-based compounds; condensation reaction-curable silicone rubber compositions comprising at least organopolysiloxanes having at least two silicone-bonded hydroxyl groups or hydrolyzable groups such as alkoxy groups, oxime groups, acetoxy groups, or aminoxy groups per molecule, silane crosslinking agents having at least three silicon-bonded hydrolyzable groups such as alkoxy groups, oxime groups, acetoxy groups, or aminoxy groups per molecule, and condensation reaction catalysts such as organic tin compounds or organic titanium compounds; and organic peroxide-curable silicone rubber compositions comprising at least a diorganopolysiloxane having at least one alkenyl group per molecule, and organic peroxides, and addition reaction-curable silicone rubber compositions are particularly preferable. This is because a silicone rubber particle formed by an addition reaction-curable silicone rubber composition is suitably used in the field of cosmetic products and the like.

Examples of methods for forming the silicone rubber particle include a method of using a pulverizer such as a grinder to pulverize the silicone rubber obtained by curing the silicone rubber composition described above; a method of spraying the silicone rubber composition with a sprayer such as a spray dryer and curing the silicone rubber composition; and a method of dispersing the silicone rubber composition in water or a surfactant aqueous solution and curing the silicone rubber composition. The method of dispersing the silicone rubber composition in water or a surfactant aqueous solution and curing the silicone rubber composition is particularly preferable, since the method can enhance the possibility of presence of greater amounts of spherical or substantially spherical particles having excellent dispersibility in paints or cosmetics. In order to prepare a water-based dispersion liquid of the silicone rubber composition, an agitator such as a colloid mill or a mixing device such as an ultrasonic vibrator may be used. Prior to preparing a water-based dispersion liquid of the silicone rubber composition, it is preferable to cool the silicone rubber composition in advance to control the curability thereof. The silicone rubber particle can be prepared by curing the silicone rubber composition in this water dispersion liquid and then removing the water from the water-based dispersion liquid. An example of a method for removing water from the water-based dispersion liquid is a method of drying using a vacuum dryer, a circulating hot air oven, or a spray dryer.

The composite silicone rubber particle of the present invention is also suitable for use as a dispersion prepared by dispersing the particle in a water-based composition. A surfactant is preferably used in order to stabilize the silicone rubber composition as a particulate in the water-based dispersion liquid. The added amount of the surfactant is preferably in the range of from 0.1 to 20 parts by weight and more preferably in the range of from 0.5 to 5 parts by weight per 100 parts by weight of the silicone rubber composition. The added amount of water is preferably in the range of from 40 to 2,000 parts by weight and particularly preferably in the range of from 40 to 1,000 parts by weight per 100 parts by weight of the silicone rubber composition. This is because when the added amount of water is less than the lower limit of the range described above, it is difficult to form a uniform water-based dispersion liquid of the silicone rubber composition, whereas when the added amount of water exceeds the upper limit of the range described above, the productivity of the silicone rubber particle is dramatically diminished.

The composite silicone rubber particle of the present invention may contain a non-crosslinked oil component, but the content is preferably not more than 10 wt % and more preferably not more than 5 wt % in the silicone rubber particle. This is because when the content exceeds the upper limit of the range described above, the fluidity of the composite silicone rubber particle tends to be diminished. The silicone rubber particle may also contain a surfactant used in the manufacturing process thereof, but the content thereof is preferably not greater than 5 wt % and more preferably not greater than 1 wt %. When the content exceeds the upper limit of the range described above, the decrease in fluidity of the composite silicone rubber particle is small.

The surface of the fine particle is modified with one or a plurality of silyl groups having a functional group containing quaternary ammonium salt.

Specific examples of the fine particle include metal oxide fine particle such as silicon oxide, titanium oxide, aluminum oxide, zirconium oxide, and antimony oxide; metal nitride fine particle such as boron nitride and aluminum nitride; metal hydroxide fine particle such as aluminum hydroxide and magnesium hydroxide; metal carbonates such as calcium carbonate; metal fine particle such as iron, silver, copper, and gold; sulfide fine particle, chloride fine particle, silsesquioxane, resinified silicone particle, and silicone rubber particle of a very small particle size so that the physical properties do not differ substantially from those of silsesquioxane. The surface of these particles may be treated to be hydrophobic in advance by organosilicon compounds such as organoalcoxysilane, organochlorosilane, organosilazane and the like. The fine particle is preferably an inorganic fine particle, more preferably a metal oxide fine particle, and even more preferably a silica fine particle. The particle may be an inorganic fine particle having an organic group on the surface layer of the fine particle, as in the case of many silsesquioxanes, and in the present disclosure, the fine particle having an organic group on the surface layer in this manner is also considered an embodiment of inorganic fine particle. A preferable silica fine particle is dry silica, examples of which include fumed silica, precipitated silica, pulverized silica, synthetic silica, and spherical silica, but a fumed silica with a small particle size is preferable. This is because a smaller particle size makes it possible to reduce the compounded amount of the composite silicone rubber particle and also facilitates a reaction with a condensate of a silicon compound. The BET specific surface area of the fumed silica is not less than 10 m²/g and preferably 50 m²/g.

The primary particle size of the fine particles is from 5 to 350 nm, and the BET specific surface area is 200 m²/g. In either case, the particle size is preferably smaller than that of the silicone rubber particles so that the silicone rubber particle can be covered.

A preferable example of the composite silicone rubber particle of the present invention is one in which the functional group containing quaternary ammonium salt is represented by the following general formula (1).

$$R^1-((N^+X^-R^2{}_2)-R^3)_a-Y \qquad (1):$$

(wherein $R^1$ is a hydrocarbon group having from 1 to 30 carbon atoms; each $R^2$ is independently a hydrogen atom or a hydrocarbon group having from 1 to 4 carbon atoms; each $R^3$ is independently selected from the group consisting of hydrocarbon groups having from 1 to 8 carbon atoms; X is a monovalent anionic group; a is an integer from 1 to 4; and Y is a divalent or higher linking group which may contain a hetero-atom bonded to the surface of the fine particle)

In the composite silicone rubber particle of the present invention, $R^1$ is preferably selected from the group consisting of hydrocarbon groups having from 1 to 26 carbon atoms, more preferably from 7 to 24 carbon atoms, and even more preferably from 12 to 22 carbon atoms. $R^1$ may be straight-chained or branched-chained but is preferably straight-chained or partially straight-chained and even more preferably straight-chained. Each $R^2$ is preferably a hydrogen atom or a hydrocarbon group having 1 or 2 carbon atoms, and a methyl group is more preferably selected. Each $R^3$ is preferably selected from the group consisting of hydrocarbon groups having from 1 to 4 carbon atoms and more preferably from 1 to 3 carbon atoms. $R^3$ may be straight-chained or branched-chained but is preferably straight-chained or partially straight-chained and even more preferably straight-chained. X is preferably a halogen group and more preferably a chloro group. In addition, a is preferably an integer of 1 or 2 and is more preferably 1. Y is a linking group bonded to the surface of the fine particle, and the linking group may form a bond with another linking group directly or via other atoms. Y preferably has a silicon atom and an oxygen atom (—O—).

The composite silicone rubber particle of the present invention may have one or more structure, in which the functional group containing quaternary ammonium salt bonds to the surface of the fine particle via a linking group containing silicon (Si), and a silicon atom in the linking group and the surface of the fine particle are bonded via an oxygen atom (—O—).

Examples of the quaternary ammonium salt contained in the composite silicone rubber particle of the present invention include octadecyldimethyl(3-trihydroxysilylpropyl)ammonium chloride, octadecyl-bis(triethoxysilylpropyl)ammonium chloride, N-trimethoxysily-lundecyl-N,N,N-tri-n-butylammonium bromide, 4-(trimethoxysilylethyl) benzyltrimethylammonium chloride, (styrylmethyl)bis(triethoxysilylpropyl)ammonium chloride, N-trimethoxysilylpropyl-N,N,N-tri-n-butylammonium bromide, N-trimethoxysilylpropyl-N,N,N-tri-n-butylammonium chloride, N-trimethoxysilylpropyl-N,N,N-trimethylammonium chloride, tetradecyl(3-trimethoxysilylpropyl) ammonium chloride, and octadecyldimethyl[3-(trimethoxysilyl)propyl]ammonium chloride. Of these, N,N,N-octadecyldimethylammonium chloride or N,N,N-trimethylammonium chloride is preferable. In addition, octadecyldimethyl[3-(trimethoxysilyl)propyl]ammonium chloride, N-trimethoxysilylpropyl-N,N,N-trimethylammonium chloride, or N-triethoxysilylpropyl-N,N,N-trimethylammonium chloride is more preferable.

In the composite silicone rubber particle of the present invention, the content of the functional group containing quaternary ammonium salt is preferably from 0.1 to 10 wt % of the weight of the entire composite silicone rubber particle. The content is more preferably from 0.3 to 9.0 wt %, even more preferably from 0.3 to 8.0 wt %, and even more preferably from 0.6 to 7.5 wt %. When the content is less than the lower limit of the range described above, the features of the composite silicone rubber particle hardly manifest, and features such as antimicrobial activity or hair adhesion are not easily demonstrated. On the other hand, when the content exceeds the upper limit of the range described above, the fluidity of the composite silicone rubber particle tends to be diminished.

These values are values calculated from the reaction ratio of the raw material, and when an excess amount of a reactive functional group is present on a surface of the fine particle such as silica, the values can be determined stoichiometrically from values calculated under the assumption that the particle is modified by the entire amount. The same assumption is applied hereafter.

The weight ratio of the functional group represented by the following general formula (1') containing quaternary ammonium salt in the composite silicone rubber particle of the present invention (functional silyl group/fine particle) is preferably from 0.03 to 0.70, more preferably from 0.05 to 0.60, and even more preferably from 0.10 to 0.50.

  General formula (1'):

(wherein R$^1$ to R$^3$, X, and a are the same as in general formula (1); and Y' is a linking group having a silicon atom bonded to an oxygen atom (—O—) on the surface of the fine particle)

This is because when the weight ratio is less than the lower limit of the range described above, the fluidity of the composite silicone rubber particle tends to be diminished, and when the weight ratio exceeds the upper limit of the range described above, the features of the composite silicone rubber particle other than the fluidity may not be demonstrated.

The content of the fine particle in the composite silicone rubber particle of the present invention (excluding the weight of the functional group in general formula (1')) is from 0.5 to 10 wt % of the entire composite silicone rubber. The content is more preferably from 0.5 to 8.0 wt % and even more preferably from 1.0 to 6.0 wt %. This is because when the content is less than the lower limit of the range described above, the fluidity of the composite silicone rubber particle is not easily improved, and when the content exceeds the upper limit of the range described above, there is a higher likelihood that the particle will be present in a state removed from the surface rather than on the surface of the composite silicone rubber particle.

Antimicrobial activity represents bactericidal activity with respect to microorganisms (including one or more types of microorganisms or multicellular organisms such as algae, mosses, or ferns selected from a wider range of microorganisms such as bacteria, fungi, yeasts, and algae, for example) when the composite silicone rubber particle of the present invention is present on an object, in a material, or in an object, and the antimicrobial activity inhibits growth of the microorganisms. Antimicrobial activity also refers to the loss of the ability for stable survival of these organisms due to adverse effects on fixation to an external object surface by such organisms. In addition, composite silicone rubber particle having antimicrobial activity may also have an antiviral effect.

The methanol content of the composite silicone rubber particle of the present invention is not greater than 1,000 ppm. The content is preferably not greater than 100 ppm, more preferably not greater than 10 ppm, and most preferably not greater than 1 ppm. This is because when methanol is contained in a cosmetic product or a skin preparation for external use in an amount greater than a certain amount, the methanol has an harmful effect on the human body.

The manufacturing method of a composite silicone rubber particle, which is one of the present inventions, will be described in detail hereinafter.

A first embodiment of the manufacturing method of a composite silicone rubber particle of the present invention has at least the following steps:

step 1: forming a composite silicone rubber particle by mixing a fine particle and a silicone rubber particle using a mechanical force; and step 2: modifying surface of the fine particle of the composite silicone rubber particle obtained in step 1 with a silicon compound having a functional group containing quaternary ammonium salt and being capable of forming a chemical bond on the surface of the fine particle.

In this first embodiment, the dispersibility can be enhanced by mixing a fine particle and a silicone rubber particle using a mechanical force to cover the surface of the silicone rubber particle with the fine particle and to form a composite silicone rubber particle. Next, the surface of the fine particle of the resulting composite silicone rubber particle is modified by a silicon compound having a functional group containing quaternary ammonium salt and being capable of forming a chemical bond on the surface of the fine particle. This makes it possible to modify the surface of the fine particle with the functional group having a silicon compound. Steps 1 and 2 may also be performed simultaneously.

A second embodiment has at least the following steps:

Step 1: modifying surface of a fine particle with a silicon compound having a functional group containing quaternary ammonium salt and being capable of forming a chemical bond on the surface of the fine particle; and step 2: forming a composite silicone rubber particle by mixing the fine particle obtained in step 1 with a silicone rubber particle using a mechanical force.

In contrast to the first embodiment, modifying only surface of the fine particle first enables an optional process on the fine particle without targeting the silicone rubber particle, which makes it easier to control the processing. In addition, the man hours and cost required to produce the composite silicone rubber particle can be reduced.

As a result, it is possible to enhance the dispersibility by covering the surface of the silicone rubber particle with the fine particle to form a composite silicone rubber particle. The functional group of the silicon compound having quaternary ammonium salt can modify the surface of the fine particle and, when methanol is generated, to easily handle the treatment thereof. In addition, by treating surface of the fine particle in advance, it becomes possible to facilitate heat treatment as an optional process and to reduce the man hours and cost required for manufacturing.

The manufacturing method of a composite silicone rubber particle of the present invention may also include a step of reducing the methanol content of the composite silicone rubber particle to not greater than 1,000 ppm after the step of modifying the surface of the fine particle in the first and second embodiments described above. In particular, this can be achieved by heating the fine particle at a temperature of 65° C. or higher.

The surface of the silicone rubber particle is covered by a hydrolysis/condensation reaction product of the silicon compound containing quaternary ammonium salt and the fine particle. In this process, surface of the silica fine particle is treated with a silicon compound having a functional group having quaternary ammonium salt or a (partial) condensate thereof, and the reaction further proceeds by heating to obtain a reaction product of a condensate and a fine particle. The reaction product of the fine particle is then mixed with the silicone rubber particle to prepare a composite silicone rubber particle. The mixing device is the same as that described above, and a dry method is also preferable over a wet method due to the simplicity of the dry method.

In this manufacturing method, the step of covering the surface of the silicone rubber particle with the fine particle may be performed with a wet method or a dry method, but a dry treatment method is preferable from the perspective of simplicity. The device for mixing these components is not limited, and examples thereof include a Henschel mixer and a super mixer. The temperature during mixing is not particularly limited, and mixing may be performed at room temperature, for example. Since a silicone rubber particle having poor fluidity demonstrates fluidity when a fine particle adheres to the surface thereof, the mixing time must be determined appropriately by observing changes in the state thereof. The manufacturing method of the second embodiment is preferable in that there is little loss of the raw material in the manufacturing process.

The step of modifying the surface of the fine particle in this manufacturing method refers to a step in which a silicon compound containing quaternary ammonium salt forms a chemical bond with a fine particle. In this step, the same processes as those of the step of covering the surface of the silicone rubber particle may be used. This is because since reactivity of the silicon compound itself is high, a reaction with the reactive groups present on the surface of the fine particle is induced when the silicon compound comes into contact with the fine particle. In one embodiment of surface modification, a silicon compound (or a (partial) condensate thereof) having a silane reacts with the fine particle having a hydroxyl group on the surface thereof. In another embodiment of the present invention, as described in the working examples, a silanol group on the silica surface and a silicon compound (or a condensate thereof) react to produce a reaction product on the surface of silica particle.

Part of the silicon compound having quaternary ammonium salt functional group used in the manufacturing of the composite silicone rubber particle of the present invention may be (partially) subjected to hydrolytic condensation. The silicon compound preferably has an alkoxy group, a hydroxyl group, an alkyl group, or an alkylene group (where at least one group is an alkoxy group) and more preferably has a methoxy group or an ethoxy group to facilitate a hydrolytic condensation reaction with a fine particle (or silicone rubber). The silicon compound preferably has a tridecyl group, a tetradecyl group, a pentadecyl group, a hexadecyl group, a heptadecyl group, an octadecyl group, a nonadecyl group, a decadecyl group, an undecadecyl group, a dodecadecyl group, a tridecadecyl group, a tetradecadecyl group, a pentadecadecyl group, or a hexadecadecyl group. Of these, the silicon compound preferably has a hexadecyl group, a heptadecyl group, an octadecyl group, a nonadecyl group, or a decadecyl group from the perspective of compatibility with the silicone rubber particle and the minimization of chemical effects on other components.

Some of the groups of the silicon compound may be chemically bonded to another silicon compound rather than the fine particle as a result of hydrolytic condensation.

Further, a preferable example of the silicon compound is represented by following general formula (2).

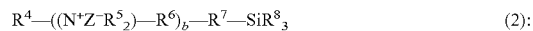

$$R^4-((N^+Z^-R^5_2)-R^6)_b-R^7-SiR^8_3 \quad (2):$$

(wherein $R^4$ is a hydrocarbon group having from 1 to 30 carbon atoms; each $R^5$ is a hydrogen atom or a hydrocarbon group having from 1 to 4 carbon atoms; each $R^6$ is a hydrocarbon group having from 1 to 8 carbon atoms; $R^7$ is a divalent organic group or a hetero-atom; each $R^8$ is an alkoxy group, a hydroxyl group, an alkyl group, or an alkylene group (where at least one $R^8$ is an alkoxy group); Z is a monovalent anionic group; and b is an integer from 1 to 4)

In the composite silicone rubber particle of the present invention, $R^4$ is preferably selected from the group consisting of hydrocarbon groups having from 1 to 26 carbon atoms, more preferably from 7 to 24 carbon atoms, and even more preferably from 12 to 22 carbon atoms. $R^4$ may be straight-chained or branched-chained but is preferably straight-chained or partially straight-chained and even more preferably straight-chained. Each $R^5$ is preferably a hydrogen atom or a hydrocarbon group having 1 or 2 carbon atoms, and a methyl group is more preferably selected. Each $R^6$ is preferably selected from the group consisting of hydrocarbon groups having from 1 to 4 carbon atoms and more preferably from 1 to 3 carbon atoms. $R^6$ may be straight-chained or branched-chained but is preferably straight-chained or partially straight-chained and even more preferably straight-chained. $R^7$ is preferably a divalent organic group or a hetero-atom and is essentially straight-chained. Each $R^8$ is an alkoxy group, a hydroxyl group, an alkyl group, or an alkylene group (where at least one $R^8$ is an alkoxy group); Z is preferably a halogen group and more preferably a chloro group. In addition, b is preferably an integer of 1 or 2 and is more preferably 1.

Examples of the quaternary ammonium salt silicon compound include octadecyldimethyl(3-trihydroxysilylpropyl) ammonium chloride, octadecyl-bis(triethoxysilylpropyl)ammonium chloride, N-trimethoxysily-lundecyl-N,N,N-tri-n-butylammonium bromide, 4-(trimethoxysilylethyl) benzyltrimethylammonium chloride, (styrylmethyl)bis (triethoxysilylpropyl)ammonium chloride, N-trimethoxysilylpropyl-N,N,N-tri-n-butylammonium bromide, N-trimethoxysilylpropyl-N,N,N-tri-n-butylammonium chloride, N-trimethoxysilylpropyl-N,N,N-trimethylammonium chloride, tetradecyl(3-trimethoxysilylpropyl) ammonium chloride, and octadecyldimethyl[3-(trimethoxysilyl)propyl]ammonium chloride. Of these, N,N,N-octadecyldimethylammonium chloride or N,N,N-trimethylammonium chloride is preferable. In addition, octadecyldimethyl[3-(trimethoxysilyl)propyl]ammonium chloride, N-trimethoxysilylpropyl-N,N,N-trimethylammonium chloride, or N-triethoxysilylpropyl-N,N,N-trimethylammonium chloride is even more preferable.

In the composite silicone rubber particle of the present invention, the content of the silicon compound having quaternary ammonium salt functional group is preferably from 0.1 to 10 wt % of the weight of the composite silicone rubber particle. The content is more preferably from 0.3 to 9.0 wt %, even more preferably from 0.3 to 8.0 wt %, and even more preferably from 0.6 to 7.5 wt %. When the content is less than the lower limit of the range described above, the features of the composite silicone rubber particle may not appear, and features such as antimicrobial activity or hair adhesion are not easily demonstrated as well. On the other hand, when the content exceeds the upper limit of the range described above, fluidity of the composite silicone rubber particle tends to be diminished.

In the manufacturing method of a composite silicone rubber particle of the present invention, the weight ratio when mixing the fine particle and the silicon compound having quaternary ammonium salt functional group (functional silane/fine particle) is preferably from 0.03 to 0.70, more preferably from 0.05 to 0.60, and even more preferably from 0.10 to 0.50. This is because when the weight ratio is less than the lower limit of the range described above, fluidity of the composite silicone rubber particle tends to be diminished, and when the silica particle exceeds the upper limit of the range described above, the features of the composite silicone rubber particle other than the fluidity are not easily demonstrated.

In the manufacturing method of a composite silicone rubber particle of the present invention, the content of the fine particle is from 0.5 to 10 wt % of the entire composite silicone rubber particle. The content is more preferably from 0.5 to 8.0 wt % and even more preferably from 1.0 to 6.0 wt %. This is because when the content is less than the lower limit of the range described above, fluidity of the composite silicone rubber particle is not easily improved, and when the content exceeds the upper limit of the range described above, there is a higher likelihood that the particle will be present in a state removed from the surface rather than on the surface of the composite silicone rubber particle.

The methanol content of the composite silicone rubber particle of the present invention is not greater than 1,000 ppm, by accommodating the heating step in the manufacturing method of the present invention. The content ratio is preferably not greater than 100 ppm, more preferably not greater than 10 ppm, and most preferably not greater than 1 ppm.

The composite silicone rubber particle of the present invention can be used as composition for cosmetic product or topical dosage form for skin.

The cosmetic of the present invention contains the composite silicone rubber particle described above. Examples of this cosmetic include washing cosmetics such as soap, body shampoo, and facial cream; foundation cosmetic products such as skin lotion, cream, milky lotion, and packs; base makeup cosmetics such as facial powder and foundation; lipstick, rouge, eye/eyebrow cosmetics such as eye shadow, eye liner, and mascara; makeup cosmetics such as manicures; hair cosmetics such as shampoo, hair rinse, hair dressing, hair tonics, hair growth promoters, and hair dyes; fragrant cosmetics such as fragrance and cologne; toothpaste; bath preparations; and special cosmetics such as hair removal products, shaving cream, antiperspirants/deodorants, and sunscreen products. Examples of the dosage form of this cosmetic include an aqueous liquid, an oily liquid, an emulsion, a cream, a foam, a semisolid, a solid, and a powder. This cosmetic may also be used in the form of a spray.

In this cosmetic, the content of the composite silicone rubber particle described above is preferably in the range of from 0.5 to 99.0 wt % and particularly preferably in the range of from 1.0 to 95 wt % in the cosmetic. This is because when the content of the composite silicone rubber particle described above exceeds the upper limit described above, the effect as a cosmetic is lost, and when the content is less than the lower limit of the range described above, it becomes difficult to enhance the feel of use of the cosmetic.

As cosmetic raw materials, the composite silicone rubber particle may also be dispersed into an aqueous phase or an oil phase using the cosmetic product components described in the following paragraph and thereafter as a media (aqueous medium or oil-based medium). As an aqueous medium, water such as purified water, ion-exchanged water, alkali ion water, deep water, wave water, and natural water; lower alcohols such as ethyl alcohol, propyl alcohol, and isopropyl alcohol; and aqueous solvents miscible with water such as polyhydric alcohols including glycerin, 1,3-butylene glycol, isoprene glycol, and dipropylene glycol can be used.

Examples of oil-based media (oil agents) include silicone oils, hydrocarbon oils, higher fatty acids, higher alcohols, ester oils (including oils and fats), ether oils, mineral oils, and fluorine oils. Of these, silicone oils, hydrocarbon oils, and ester oils are more preferable from the perspective of the feel of use. Specific examples include silicone oils such as dimethylpolysiloxane, methylhydrogenpolysiloxane, methylphenylpolysiloxane, polyether-modified organopolysiloxane, fluoroalkyl/polyoxyalkylene-comodified organopolysiloxane, alkyl-modified organopolysiloxane, terminal-modified organopolysiloxane, fluorine-modified organopolysiloxane, amodimethicone, amino-modified organopolysiloxane, acryl silicone, and trimethylsiloxysilicic acid, hydrocarbon oils such as liquid paraffin, vaseline, and squalane, and ester oils such as myristyl myristate, hexyl laurate, decyl oleate, isopropyl myristate, hexyldecyl dimethyloctanoate, glycerin monostearic acid, diethyl phthalate, ethylene glycol monostearate, octyl oxystearate, isononyl isononanoate, and isotridecyl isononanoate. One or more types of oil agents may be used. The content of the oil agent with respect to the entire water-in-oil emulsion cosmetic used in the present invention is preferably from 10 to 50 wt % and more preferably from 20 to 40 wt % from the perspective of the feel of use and storage stability.

Following other components generally used in cosmetics may be added to the cosmetic of the present invention, provided that such components do not inhibit effectiveness of the present invention: water, coloring agents, alcohols, water-soluble polymers, film-forming agents, oil agents, oil-soluble gelling agents, organo-modified clay minerals, surfactants, resins, salts, moisturizing agents, preservatives, antimicrobial agents, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and fragrances. However, the additives are not particularly limited to thereto. The content of each of these cosmetic components, excluding water, is preferably within the range of from 0.5 to 99.0 wt % and particularly preferably within the range of from 1.0 to 95 wt % in the cosmetic. This is because when the content of one of the cosmetic components exceeds the upper limit of the range described above, the feel of use as a cosmetic is not preferable. When added, if the content is less than the lower limit of the range described above, effects such as the enhancement of the feel of use of the cosmetic become difficult to achieve. The cosmetic components and the compounded amounts thereof disclosed in Japanese Unexamined Patent Application Publication No. 2015-113303A are included here for reference.

The water is clean and free of components that are harmful to the human body, and examples thereof include tap water, purified water, mineral water, and deep sea water. When the cosmetic of the present invention is water-based, water-soluble additional components may be optionally compounded into the aqueous phase within a range that does not diminish the effect of the present invention. In addition, a known pH adjusting agent, preservative, antimicrobial agent, or antioxidant may also be compounded appropriately with the objective of enhancing the storage stability or the like of the cosmetic.

Examples of coloring agents include inorganic red pigments such as red iron oxide, iron oxide, iron hydroxide, and iron titanate, inorganic brown pigments such as γ-iron oxide, inorganic yellow pigments such as yellow iron oxide and ocher, inorganic black pigments such as black iron oxide and carbon black, inorganic purple pigments such as manganese violet and cobalt violet, inorganic green pigments such as chromium hydroxide, chromium oxide, cobalt oxide, and cobalt titanate, inorganic blue pigments such as iron blue and ultramarine blue, organic pigments such as pigments prepared by raking a tar-based coloring matters such as red No. 3, red No. 104, red No. 106, red No. 201, red No. 202, red No. 204, red No. 205, red No. 220, red No. 226, red No. 227, red No. 228, red No. 230, red No. 401, red No. 505, yellow No. 4, yellow No. 5, yellow No. 202, yellow No. 203, yellow No. 204, yellow No. 401, blue No. 1, blue No. 2, blue No. 201, blue No. 404, green No. 3, green No. 201, green No. 204, green No. 205, orange No. 201, orange No. 203, orange No. 204, orange No. 206, and orange No. 207, and pigments prepared by raking natural coloring matters such as carminic acid, laccaic acid, carthamin, brazilin, and crocin; pearl pigments such as titanium oxide-covered mica, titanated mica, iron oxide-treated titanated mica, titanium oxide-covered mica, bismuth oxychloride, titanium oxide-covered bismuth oxychloride, titanium oxide-covered talc, fish scales, and titanium oxide-covered colored mica; and metal powders such as aluminum, gold, silver, copper, platinum, and stainless steel.

These coloring agents are preferably subjected to water-repellent treatment. A composition prepared by combining these coloring agents with one another or a composition subjected to surface treatment with a general oil agent, silicone compound, fluorine compound, or surfactant may also be used, and One or more types may be used as necessary.

Examples of such water-repellent treatments include treatments in which the coloring agent is treated with various water repellent agents such as octylsilane. Specific examples thereof include organosiloxane treatments such as a methylhydrogenpolysiloxane treatment, a silicone resin treatment, a silicone rubber treatment, an acryl silicone treatment, a fluorinated silicone treatment, and the like; metallic soap treatments such as a zinc stearate treatment and the like; silane treatments such as a silane coupling agent treatment, an alkylsilane treatment, and the like; fluorine compound treatments such as a perfluoroalkylsilane treatment, a perfluoroalkyl phosphate treatment, a perfluoro polyether treatment, and the like; amino acid treatments such as an N-lauroyl-L-lysine treatment and the like; oil agent treatments such as a squalane treatment and the like; and acryl treatments such as an alkyl acrylate treatment and the like. One or more of the treatments described above can be used be in combination.

One or more types selected from lower alcohols, sugar alcohols and higher alcohols can be used as alcohols. Specific examples include lower alcohols such as ethanol and isopropanol; sugar alcohols such as sorbitol and maltose; and higher alcohols such as lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), and monooleyl glycerol ether (selachyl alcohol).

A water-soluble polymer is compounded for the purpose of enhancing the feel of use of the cosmetic, and any amphoteric, cationic, anionic, non-ionic, or water-swellable clay mineral may be used as an aqueous polymer as long as it is a substance used in ordinary cosmetics, and One or more types of aqueous polymers may also be used in combination. These aqueous polymers have a thickening effect on hydrous components and are therefore useful for obtaining a gel-like hydrous cosmetic, a water-in-oil emulsion cosmetic, or an oil-in-water emulsion cosmetic. Some of the water-soluble polymers may also be used as surfactants.

Specific examples of amphoteric water-soluble polymers include amphoteric starch, dimethyldiallylammonium chloride derivatives (for example, copolymers of acrylamide, acrylic acid, and dimethyldiallylammonium chloride, and copolymers of acrylic acid and dimethyldiallylammonium chloride), and methacrylic acid derivatives (for example, polymethacryloyl ethyl dimethyl betaine, N-methacryloyloxy ethylN,N-dimethylammonium-α-methyl carboxybetaine/alkyl methacrylate copolymers, and the like).

Examples of cationic water-soluble polymers include quaternary nitrogen-modified polysaccharides (for example, cation-modified cellulose, cation-modified hydroxyethylcellulose, cation-modified guar gum, cation-modified locust bean gum, cation-modified starch, and the like); dimethyldiallylammonium chloride derivatives (for example, copolymers of dimethyldiallylammonium chloride and acrylamide, polychlorinated dimethylmethylene piperidinium, and the like); vinylpyrrolidone derivatives (for example, copolymer salts of vinylpyrrolidone and dimethylaminoethyl methacrylic acid, copolymers of vinylpyrrolidone and methacrylamide propyltrimethylammonium chloride, copolymers of vinylpyrrolidone and methylvinylimidazolium chloride, and the like); methacrylic acid derivatives (for example, copolymers of methacryloyl ethyl dimethyl betaine, methacryloyl ethyl trimethyl ammonium chloride, and 2-hydroxyethyl methacrylate, copolymers of methacryloyl ethyl dimethyl betaine, methacryloyl ethyl trimethyl ammonium chloride, and methoxypolyethylene glycol methacrylate, and the like).

Examples of anionic water-soluble polymers include polyacrylic acids or alkali metal salts thereof, polymethacrylic acids or alkali metal salts thereof, hyaluronic acid or alkali metal salts thereof, acetylated hyaluronic acid or alkali metal salts thereof, and aliphatic carboxylic acids such as hydrolysates of methyl vinyl ether/maleic anhydride copolymers or water-soluble polymers of metal salts thereof, carboxymethylcellulose or alkali metal salts thereof, methyl vinyl ether/maleic acid half ester copolymers, acrylic resin alkanolamine solutions, and carboxyvinyl polymers.

Examples of nonionic water-soluble polymers include natural polymer compounds such as polyvinyl pyrrolidone, highly-polymerized polyethylene glycol, vinyl pyrrolidone/vinylacetate copolymers, vinyl pyrrolidone/dimethylamino ethyl methacrylate copolymers, vinyl caprolactam/vinyl pyrrolidone/dimethylamino ethyl methacrylate copolymers, cellulose or derivatives thereof (for example, methyl-cellulose, ethylcellulose, hydroxyethylcellulose, hydroxypropylcellulose, and carboxymethylcellulose), keratin and collagen or derivatives thereof, calcium alginate, pullulan, agar, gelatin, tamarind seed polysacharides, xanthan gum, carrageenan, high-methoxyl pectin, low-methoxyl pectin, guar gum, pectin, gum arabic, crystalline cellulose, arabinogalactan, karaya gum, tragacanth gum, alginic acid, albumin, casein, curdlan, gellan gum, dextran, quince seed gum, gum tragacanth, chitin/chitosan derivatives, starch (rice, corn, potatoes, wheat, and the like), and keratin and collagen or derivatives thereof.

A water-swellable clay mineral is an inorganic water-soluble polymer, which is a type of a colloid-containing aluminum silicate having a three-layer structure; examples of which typically include compositions represented by the following formula (A):

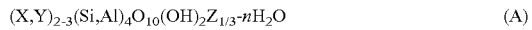

(A)

(wherein X is Al, Fe (III), Mn (III), or Cr (III); Y is Mg, Fe (II), Ni, Zn, or Li; and Z is K, Na, or Ca). Specific examples of such inorganic water-soluble polymers include bentonite, montmorillonite, beidellite, nontronite, saponite, hectorite, aluminum magnesium silicate, and silicic anhydride, and these may be used as natural products or synthetic products.

Examples of silicone oils include cyclic organopolysiloxanes such as hexamethyl cyclotrisiloxane (D3), octamethyl cyclotetrasiloxane (D4), decamethyl cyclopentasiloxane (D5), dodecamethyl-cyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl) trimethylcyclotrisiloxane, 1,3,5,7-tetra(3-methacryloxypropyl) tetramethyl cyclotetrasiloxane, 1,3,5,7-tetra(3-acryloxypropyl) tetramethyl cyclotetrasiloxane, 1,3,5,7-tetra(3-carboxypropyl) tetramethyl cyclotetrasiloxane, 1,3,5,7-tetra(3-vinyloxypropyl) tetramethyl cyclotetrasiloxane, 1,3,5,7-tetra(p-vinylphenyl) tetramethyl cyclotetrasiloxane, 1,3,5,7-tetra[3-(p-vinylphenyl) propyl] tetramethyl cyclotetrasiloxane, 1,3, 5,7-tetra(N-acryloyl-N-methyl-3-aminopropyl) tetramethyl cyclotetrasiloxane, 1,3,5,7-tetra(N,N-bis (lauroyl)-3-aminopropyl) tetramethyl cyclotetrasiloxane, and the like. Examples of straight organopolysiloxanes include dimethylpolysiloxane in which both molecular terminals are capped with trimethylsiloxy groups (dimethylsilicone with a low viscosity such as 2 cst or 6 cst to dimethylsilicone with a high viscosity such as 1,000,000 cst), organohydrogenpolysiloxane, methylphenylpolysiloxane in which both molecular terminals are capped with trimethylsiloxy groups, a copolymer of methylphenylsiloxane and dimethylsiloxane in which both molecular terminals are capped with trimethylsiloxy groups, diphenylpolysiloxane in which both molecular terminals are capped with trimethylsiloxy groups, a copolymer of diphenylsiloxane and dimethylsiloxane in which both molecular terminals are capped with trimethylsiloxy groups, trimethylpentaphenyltrisiloxane, phenyl (trimethylsiloxy) siloxane, methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl (3,3,3-trifluoropropyl) siloxane and dimethylsiloxane in which both molecular terminals are capped with trimethylsiloxy groups, α,ω-dihydroxypolydimethylsiloxane, α,ω-diethoxypolydimethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, a higher alkoxy-modified silicone, a higher fatty acid-modified silicone, and the like.

Examples of the hydrocarbon oil include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, micro-crystalline wax, paraffin wax, polyethylene wax, polyethylene/polypropylene wax, squalane, squalene, pristane, polyisoprene, and the like.

Examples of ester oils include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthlate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethylolpropane (isostearate/sebacate), trimethylolpropane trioctanoate, trimethylopropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyl dodecyl gum ester, ethyl oleate, octyldodecyl oleate, neopentyl glycol dicaprylate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldecyl N-lauroyl-L-glutamate ester, di(cholesteryl/behenyl/octyldodecyl)-N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, N-lauroylsarcosine isopropyl, diisostearyl malate, neopentyl glycol dioctanoate, isodecyl neopentanoate, isotridecyl neopentanoate, isostearyl neopentanoate, isononyl isononanoate, isotridecyl isononanoate, octyl inonanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, hydrogenated rosin pentaerythrityl, pentaerythrityl triethylhexanoate, dipentaerythrityl (hydroxystearate/stearate/rosinate), polyglyceryl tetraisostearate, polyglyceryl-10 non-aisostearate, polyglyceryl-8 deca(erucate/isostearate/ricinoleate), diglyceryl (hexyldecanoate/sebacate) oligoester, glycol distearate (ethylene glycol distearate), diisopropyl dimerdilinoleate, diisostearyl dimerdilinoleate, di(isostearyl/phytosteryl)dimerdilinoleate, (phytosteryl/behenyl) dimerdilinoleate, (phytosteryl/isostearyl/cetyl/stearyl/behenyl)dimerdilinoleate, dimerdilinoleyl dimerdilinoleate, dimerdilinoleyl diisostearate, dimerdilinoleyl hydrogenated rosin condensate, dimerdilinoleic acid-curable castor oil, hydroxyalkyl dimerdilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri (caprylate/caprate/myristate/stearate), hydrogenated rosin triglyceride (hydrogenated ester gum), rosin triglyceride (ester gum), glyceryl behenate eicosadioate, glyceryl di-2-heptylundecanoate, diglyceryl myristate iostearate, cholesteryl acetate, cholesteryl nonanoate, cholesteryl stearate, cholesteryl isostearate, cholesteryl oleate, cholesteryl 12-hydroxystearate, macadamia nut oil fatty acid cholestearyl, macadamia nut of fatty acid phytosteryl, pytosteryl isostearate, soft lanolin fatty acid cholesteryl, hard lanolin fatty acid cholesteryl, long-chain branched fatty acid cholesteryl, long-chain α-hydroxy fatty acid cholesteryl, octyldodecyl ricinoleate, lanolin fatty acid octyldodecyl, octylcodecyl erucate, isostearic acid-curable castor oil, avocado oil fatty acid ethyl, and lanolin fatty acid isopropyl.

Examples of natural animal or plant fats and oils and semi-synthetic fats and oils include avocado oil, linseed oil, almond oil, ibota wax, perilla oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil, and the like. Herein, "POE" means "polyoxyethylene".

Examples of higher fatty acids include lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glycerol ether (selachyl alcohol), and the like.

Examples of fluorine-based oil agents include perfluoropolyether, perfluorodecalin, perfluorooctane, and the like, and One or more types of these oil agents may be used as necessary.

Examples of oil-soluble gelling agents include metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate, dextrin stearate, and dextrin 2-ethylhexanoate palmitate; sucrose fatty acid esters such as sucrose palmitate and sucrose stearate; fructooligosaccharide fatty acid esters such as inulin stearic acid esters and fructooligosaccharide-2-ethylhexanoate, benzylidene derivatives of sorbitol such as monobenzylidene sorbitol and dibenzylidene sorbitol; and organo-modified clay minerals such as dimethylbenzyl dodecylammonium montmorillonite clay and dimethyl dioctadecylammonium montmorillonite clay. One or more types of these agents may be used as necessary.

One or more types of surfactants selected from the group consisting of silicone-based surfactants, anionic surfactants, cationic surfactants, nonionic surfactants, amphoteric surfactants, and semipolar surfactants may be used in combination as surfactants.

Silicone-based surfactants are often used as components for oil agent emulsion or washing or for the dispersion or surface treatment of powders, and typical examples include polyglyceryl-modified silicones, glyceryl-modified silicones, sugar-modified silicones, fluorine polyether-modified silicones, polyether-modified silicones, carboxylic acid-modified silicones, sugar-modified silicones, straight-chain silicone/polyether block copolymers (polysilicone-13 and the like), and long-chain alkyl/polyether co-modified silicones.

Examples of anionic surfactants include saturated or unsaturated fatty acid salts (e.g. sodium laurate, sodium stearate, sodium oleate, sodium linolenate, and the like); alkyl-sulfuric acid salts; alkylbenzene sulfonic acids (e.g. hexylbenzenesulfonic acid, octyl-benzenesulfonic acid, dodecylbenzenesulfonic acid, and the like) and salts thereof; polyoxyalkylene alkyl ether sulfates; polyoxyalkylene alkenyl ether sulfate; polyoxyethylene alkylsulfate; alkyl sulfosuccinate salts; polyoxyalkylene sulfosuccinate salts; polyoxyalkylene alkylphenyl ether sulfate; alkanesulfonate salts; octyltrimethylammonium hydroxide; dodecyltrimethylammonium hydroxide; alkyl sulfonates; polyoxyethylene alkylphenyl ether sulfate salts; polyoxyalkylene alkyl ether acetate salts; alkyl phosphate salts; polyoxyalkylene alkyl ether phosphate salts; acylglutamate salts; α-acylsulfonate salts; alkylsulfonate salts; alkylallylsulfonate salts; α-olefinsulfonate salts; alkylnaphthalene sulfonate salts; alkanesulfonate salts; alkyl- or alkenylsulfate salts; alkylamide sulfate salts; alkyl- or alkenyl phosphate salts; alkylamide phosphate salts; alkyloylalkyl taurinate salts; N-acylamino acid salts; sulfosuccinate salts; alkyl ether carboxylate salts; amide ether carboxylate salts; α-sulfofatty acid ester salts; alanine derivatives; glycine derivatives; and arginine derivatives. Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl co-laminoformyl methylpyridinium chloride, cetylpyridinium chloride, tall oil alkylbenzyl hydroxyethylimidazolinium chloride, and benzylammonium salt.

Examples of nonionic surfactants include polyglyceryl diisostearate, diglyceryl polyhydroxystearate, isostearyl glyceryl ethers, polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl phenyl ethers, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethyleneglycol, polyoxyethylene-polyoxypropylene block polymers, alkyl polyoxyethylene-polyoxypropylene block polymer ethers, polyoxyethylene-polyoxypropylene block polymers, alkyl polyoxyethylene-polyoxypropylene block polymer ethers, and fluorine-based surfactants.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specifically, imidazoline-type amphoteric surfactants such as sodium 2-undecyl-N,N,N-(hydroxyethylcarboxymethyl)-2-imidazoline, 2-cocoyl-2-imidazolinium hydroxide-1-carboxyethyloxy disodium salt, and the like; alkylbetaine-type amphoteric surfactants such as lauryl dimethylaminoacetic betaine, myristyl betaine, and the like; amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric acid amidopropyl dimethylamino acetic acid betaine, myristic acid amidopropyl dimethylamino acetic acid betaine, palmitic acid amidopropyl dimethylamino acetic acid betaine, stearic acid amidopropyl dimethylamino acetic acid betaine, oleic acid amidopropyl dimethylamino acetic acid betaine, and the like; alkylsulfobetaine-type amphoteric surfactants such as coconut oil fatty acid dimethyl sulfopropyl betaine and the like; alkyl hydroxy sulfobetaine-type amphoteric surfactants such as lauryl dimethylaminohydroxy sulfobetaine and the like; phosphobetaine-type amphoteric surfactants such as laurylhydroxy phosphobetaine and the like; and amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbons, alkoxyethyl dihydroxyethylamine oxides having from 8 to 18 carbons, and the like are preferably used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

Examples of salts include inorganic salts, organic acid salts, amine salts, and amino acid salts. Examples of inorganic salts include sodium salts, potassium salts, magnesium salts, calcium salts, aluminum salts, zirconium salts, and zinc salts of inorganic acids such as hydrochloric acid, sulfuric acid, carbonic acid, and nitric acid. Examples of organic acid salts include salts of organic acids such as acetic acid, dehydroacetic acid, citric acid, malic acid, succinic acid, ascorbic acid, and stearic acid. Examples of amine salts and amino acid salts include salts of amines such as triethanolamine and salts of amino acids such as glutamic acid. In addition, salts of hyaluronic acid, chondroitin sulfuric acid, and the like, aluminum zirconium glycine complexes, acid-alkali neutralizing salts used in cosmetic product treatment, and the like may also be used.

Examples of moisturizing agents include polyhydric alcohols such as glycerin, sorbitol, propylene glycol, dipropylene glycol, 1,3-butylene glycol, glucose, xylitol, maltitol, and polyethylene glycol; hyaluronic acid, chondroitin sulfate, pyrrolidone carboxylate, polyoxyethylene methyl glucoside, polyoxypropylene methyl glucoside, and PEG/PPG dimethyl ethers.

Examples of preservatives include paraoxybenzoic acid alkyl esters, benzoic acid, sodium benzoate, sorbic acid, potassium sorbate, and phenoxyethanol. Examples of antimicrobial agents include benzoic acid, salicylic acid, phenol, sorbic acid, paraoxybenzoic acid alkyl esters, parachlorometacresol, hexachlorophene, benzalkonium chloride, chlorhexidine, trichlorocarbanilide, triclosan, photosensitive elements, and phenoxyethanol. In the case of rouge, the composition preferably does not contain a preservative.

Examples of antioxidants include tocopherol, butylhydroxyanisole, dibutylhydroxytoluene, and phytic acid.

Examples of pH adjusting agents include lactic acid, citric acid, glycolic acid, succinic acid, tartaric acid, dl-malic acid, potassium carbonate, sodium hydrogen carbonate, and ammonium hydrogen carbonate.

Examples of chelating agents include alanine, sodium salts of edetic acid, sodium polyphosphate, sodium metaphosphate, and phosphoric acid.

Examples of refreshing agents include L-menthol and camphor, and examples of anti-inflammatory agents include allantoin, glycyrrhetic acid, glycyrrhizinic acid, tranexamic acid, and azulene.

Examples of skin-beautifying agents include skin-lightening agents such as placenta extract, arbutin, glutathione, and saxifraga sarmentosa extract; cell activating agents such as royal jelly; rough skin improving agents; circulation promoters such as nonanoic acid valenylamide, benzyl nicotinate, β-butoxyethyl nicotinate, capsaicin, jingeron, cantharis tincture, ichthammol, caffeine, tannic acid, α-borneol, tocopherol nicotinate, inositol hexanicotinate, cyclandelate, cinnalysine, tolazoline, acetylcholine, verapamil, cepharanthine, and γ-oryzanol; skin astringents such as zinc oxide and tannic acid; antiseborrheic agents such as sulfur and thianthol. Examples of vitamins include vitamin A such as vitamin A oil, retinol, retinol acetate, and retinol palmitate; vitamin B2 such as riboflavin, riboflavin butyrate, and flavin adenine nucleotide; vitamin B6 such as pyridoxine hydrochloride, pyridoxine dioctanoate, and pyridoxine tripalmitate; vitamin B such as vitamin B12 and derivatives thereof, vitamin B15 and derivatives thereof; vitamin C such as L-ascorbic acid, L-ascorbyl dipalmitate L-ascorbyl-2-sodium sulfate, and L-ascorbyl phosphate diester dipotassium; vitamin D such as ergocalciferol and cholecalciferol; vitamin E such as α-tocopherol, β-tocopherol, γ-tocopherol, dl-α-tocopherol acetate, dl-α-tocopherol nicotinate, and dl-α-tocopherol succinate; vitamin H; vitamin P; nicotinic acids such as nicotinic acid and benzyl nicotinate; and pantothenic acids such as calcium pantothenate, D-pantothenyl alcohol, pantothenyl ethyl ether, and acetylpantothenyl ethyl ether.

Examples of amino acids include amino acids such as glycine, valine, leucine, isoleucine, serine, threonine, phenylalanine, arginine, lysine, aspartic acid, glutamic acid, cystine, cysteine, methionine, and tryptophan and/or salts thereof.

An example of a nucleic acid is deoxyribonucleic acid, and examples of hormones include estradiol and ethenyl estradiol.

A bioactive component is a substance which provides certain bioactivity to skin or hair when applied to the skin or hair; an example of which is a lipophilic component. Examples include anti-inflammatory agents, anti-aging agents, tightening agents, hair regrowth agents, hair growth promoters, moisturizing agents, circulation promoters, drying agents, warming agents, vitamins, wound healing accelerators, irritation mitigation agents, analgesics, cell activating agents, and enzyme components. Similarly, the composition may also preferably contain natural plant extract components, seaweed extract components, and/or herbal medicine components.

Pharmaceutical active ingredient is a substance which has a therapeutic effect; the example include proteins, peptides, and low-molecular-weight compounds.

Fragrances are not particularly limited as long as the fragrances are lipophilic, and examples include fragrances extracted from the flowers, seeds, leaves, roots, or the like of various plants, fragrances extracted from seaweeds, fragrances extracted from various sites or secretions of animals (for example, musks or sperm whales), and artificially synthesized fragrances (for example, menthol, musk, acetic acid esters, and vanilla). Fragrances are compounded in order to impart the cosmetic with an aroma or fragrance.

Examples of coloring matters include oil-soluble dyes, extender pigments, inorganic pigments, organic pigments, and lipophilic optical brighteners.

The cosmetic product of the present invention can be produced easily by simply uniformly mixing the cosmetic product raw materials of the present invention described above and other cosmetic product raw materials. Various mixing devices and kneading devices ordinarily used in the manufacturing of cosmetic products may be used as a mixing means. Examples of these devices include a homomixer, a paddle mixer, a Henschel mixer, a homo-disper, a colloid mill, a propeller stirrer, a homogenizer, an in-line continuous emulsifier, an ultrasonic emulsifier, and a vacuum kneader.

EXAMPLES

Present invention will be described more specifically using examples, but it is not limited only to these working examples. Note that the viscosity in the examples is the value at 25° C.

A composite silicone rubber particle was produced in the working examples and comparative examples. The content ratio (wt %) of functional silane, the content ratio (wt %) of silica, and the weight ratio of functional silane and silica in the same particle were confirmed for the composite silicone rubber particle by calculation and from solid NMR, and the average particle size, hydrophilicity, fluidity, methanol content ratio, and antimicrobial activity were measured.

Working Example 1

First, 0.5970 g of silica (Aerosil 200 produced by Nippon Aerosil Co., Ltd., dry silica, average primary particle size: 5 to 15 nm, silanol density: 4.2/100 Å$^2$, BET specific surface area: 200 m$^2$/g) and 20.2954 g of addition-curable crosslinked silicone rubber particle (average primary particle size: 5 to 10 um, JIS-A hardness: 60, containing 1 part by mass (wt %) of silicone oil) were charged into a high-speed stirrer. The components were stirred and mixed for approximately one minute at approximately 10,000 rpm. Next, 0.1974 g of a 50% methanol solution of octadecyl dimethyl[3-(trimethoxysilyl)propyl]ammonium chloride (called a "methanol solution of silane" hereafter) was added to the mixture and further stirred and mixed for approximately two minutes at approximately 10,000 rpm. The mixture was heat-treated for two hours in an oven at 120° C., and the methanol was volatilized to react silica and silane.

Working Example 2

A composite silicone rubber particle was prepared in the same manner as in Working Example 1 with exception that the amount of silica was changed to 0.4049 g, the amount of the methanol solution of silane was changed to 0.2229 g, and the amount of silicone rubber particle was changed to 20.1310 g.

Working Example 3

A composite silicone rubber particle was prepared in the same manner as in Working Example 1 with exception that the amount of silica was changed to 0.4187 g, the amount of the methanol solution of silane was changed to 0.3977 g, and the amount of silicone rubber particle was changed to 20.5924 g.

In Working Examples 4 to 7, in contrast to Working Examples 1 to 3, silane treatment was first performed on the silica.

Working Example 4

First, 4.0276 g of silica (Aerosil 200 produced by Nippon Aerosil Co., Ltd., dry silica, average primary particle size: 5 to 15 nm, silanol density: 4.2/100 Å$^2$, BET specific surface area: 200 m$^2$/g) was charged into a high-speed stirrer, and 1.954 g of a 50% methanol solution of octadecyl dimethyl [3-(trimethoxysilyl)propyl]ammonium chloride was added to the silica and stirred and mixed for approximately two minutes at approximately 10,000 rpm. The mixture was heat-treated for two hours in an oven at 120° C., and the methanol was volatilized to react silica and silane. This is referred to as the reaction product (2) of a silane condensate and fine particulate silica. A composite silicone rubber particle was prepared in the same manner as in Working Example 1 with the exception that silane was not used and that 0.4091 g of the reaction product (1) of the silane condensate and fine particulate silica and 20.1415 g of the silicone rubber particle were used.

Working Example 5

A product was prepared in the same manner as in the preparation of the reaction product (1) of a silane condensate and fine particulate silica in Working Example 4 with the exception that the charged amount of silica was 4.0427 g and the added amount of the 50% methanol solution of octadecyl dimethyl[3-(trimethoxysilyl)propyl]ammonium chloride was 3.9358 g. This was prepared as the reaction product (2) of a silane condensate and fine particulate silica.

A composite silicone rubber particle was prepared in the same manner as in Working Example 1 with the exception that silane was not used and that 0.4091 g of the reaction product (2) of the silane condensate and fine particulate silica and 20.1415 g of the silicone rubber particle were used.

Working Example 6

A composite silicone rubber particle was prepared in the same manner as in Working Example 1 with the exception that silane was not used and that 0.6138 g of the reaction product (2) of the silane condensate of Working Example 5 and fine particulate silica and 20.2914 g of the silicone rubber particle were used.

Working Example 7

A product was prepared in the same manner as in the preparation of the reaction product (1) of a silane condensate and fine particulate silica in Working Example 4 with exception that the charged amount of silica was 6.1560 g and that a mixed solution of 3.1608 g of trimethyl[3-(triethoxysilyl)propyl]ammonium chloride and 1.6208 g of ethanol was used instead of trimethyl[3-(triethoxysilyl)propyl]ammonium chloride. This is referred to as the reaction product (3) of a silane condensate and fine particulate silica.

A composite silicone rubber particle (A) was prepared in the same manner as in Working Example 1 with exception that silane was not used and that 0.6111 g of the reaction product (3) of the silane condensate and fine particulate silica and 20.5776 g of the silicone rubber particle were used.

Comparative Example 1

A composite silicone rubber particle was prepared in the same manner as in Working Example 1 with exception that silica was not mixed, that 20.1233 g of the silicone rubber particle was charged into a high-speed stirrer (opening diameter: 10 cm, depth: 5 cm), and the amount of silicone rubber particle was 20.1233 g after 0.4103 g of a 50% methanol solution of octadecyl dimethyl[3-(trimethoxysilyl) propyl]ammonium chloride was added to the mixture. The components were stirred and mixed for approximately two minutes at approximately 10,000 rpm. The mixture was transferred to a 200 mL beaker and heat-treated for two hours in a nitrogen oven at 120° C., and the methanol was volatilized to condense-react silane. The composite silicone rubber particle having this n-octadecyl dimethylammonium chloride group demonstrated strong aggregability and formed clumps of several cm in the 200 mL beaker. The clumps did not become fine even when crushed with the fingers, so the clumps were pulverized to a particle size of not greater than 1 mm with a mortar. The average particle size after pulverization exceeded the upper measurement limit of the measurement instrument, so the average particle size was presumed to be not less than 200 um.

Comparative Example 2

First, 0.6195 g of the same silica as in Working Example 1 and 21.0718 g of the same addition-curable-crosslinked silicone rubber particle as used in Working Example 1 were added into a high-speed stirrer (same as in Working Example 1). The components were stirred and mixed for approximately two minutes at approximately 10,000 rpm. A powder demonstrating fluidity was obtained. This was used as Comparative Example 2.

Comparative Example 3

The mixture of Working Example 1 prior to heat treatment was used as Comparative Example 3.

Comparative Example 4

The addition-curable crosslinked silicone rubber particle of Working Example 1 (average particle size: 14 um, JIS-A hardness: 60, containing 1 mass % of silicone oil) was used as Comparative Example 4.

Performance evaluations were performed on the silicone rubber particle obtained in Working Examples 1 to 7 and Comparative Examples 1 to 4 with regard to fluidity, dispersibility, antimicrobial activity, and methanol content.

<Methanol Content, Methanol Generation>

Approximately 0.85 g of a sample was weighed in a 20 mL vial. After the vial was heated for 30 minutes at 80° C. with a Headspace Sampler, a syringe with which 1 mL of air was aspirated from the Headspace of the vial and the air was injected into a gas chromatograph and measured. The concentration was calculated from a calibration curve created based on the added amount of methanol.

<Average Particle Size>

Using ethanol as a dispersing medium, the particle size of the composite silicone rubber particle was measured with a laser diffraction-type particle size distribution analyzer (LA-750 produced by Horiba, Ltd.), and the median diameter was used as the average particle size.

<Hydrophilicity>

First, 3.0 g of the composite silicone rubber particle was added to 100 g of water and 3 g of ethanol and stirred, and the mixture was stirred for one minute at 1,000 rpm with a homo-disper. It was observed whether the particle was dispersed as a fine particle, whether the particle was not dispersed into a fine particle but aggregated, or whether the particle was separated from water. Uniform dispersion was evaluated as Good indicating "hydrophilic"; aggregate particles were evaluated as CA (Conditionally Acceptable) indicating "slightly hydrophilic"; and cases of separation were evaluated as NA (Not Acceptable) indicating "hydrophobic".

<Fluiditity>

Approximately 20 g of the prepared modified silicone particle was placed in a polyethylene bag (opening: 15 cm), and after the particle was collected at the bottom of the bag, the fluidity was assessed based on whether the particle flowed and the shape of the particulate aggregate collapsed when the bag was rotated by 90 degrees. Cases in which the shape collapsed were evaluated as Good indicating "fluid"; and cases in which the shape did not collapse were evaluated as NA (Not Acceptable) indicating "not fluid".

<Antimicrobial Activity Test>

An antimicrobial test was performed in accordance with ASTM E2149-10: "Standard Test Method for Determining the Antimicrobial activity of Immobilized Antimicrobial Agents Under Dynamic Contact Conditions". A 5 mL mixture of either *Escherichia coli* (operating bacterial concentration: $5.48 \times 10^6$ cfu/mL) or *Staphylococcus aureus* (operating bacterial concentration: $9.5 \times 10^6$ cfu/mL) and 1 g of silicone rubber particle was shaken for 24 hours, and a 1 mL sample thereof was mixed with a sterilizing diluent to prepare diluted solutions of various concentrations. The CFUs (colony forming units) of the diluted solutions after 40 hours (28 to 30° C.) were counted, and the logarithmic rates of decrease were compared.

TABLE 1

| Experimental Examples | Working Examples | | | | | | |
|---|---|---|---|---|---|---|---|
| | 1 | 2 | 3 | 4 | 5 | 6 | 7 |
| Average diameter (μm) | 6.72 | 6.77 | 6.76 | 6.77 | 6.8 | 6.78 | 6.8 |
| Hydrophilicity | Good | Good | Good | Good | Good | Good | Good |
| Fluidity | Good | Good | Good | Good | Good | Good | Good |
| Functional silane (wt %) | 0.38 | 0.44 | 0.76 | 0.33 | 0.48 | 0.83 | 0.63 |
| Silica (wt %) | 2.85 | 1.96 | 1.98 | 1.67 | 2.47 | 2.11 | 2.26 |
| Functional silane/silica | 0.13 | 0.22 | 0.38 | 0.19 | 0.19 | 0.39 | 0.48 |
| Methanol content ratio (ppm) | <1 | <1 | <1 | <1 | <1 | <1 | <1 |
| Logarithmic rate of decrease (*Escherichia coli*) | 0.04 | 2.57 | >6 | 0.71 | 1.3 | >6 | — |
| Logarithmic rate of decrease (*Staphylococcus aereus*) | 1.17 | >5 | >5 | 2.4 | >5 | >5 | — |

| Experimental Examples | Comparative Examples | | | |
|---|---|---|---|---|
| | 1 | 2 | 3 | 4 |
| Average diameter (μm) | >200 | 6.77 | — | 13.54 |
| Hydrophilicity | Good | NA | Good | NA |
| Fluidity | CA | Good | Good | NA |
| Functional silane (wt %) | 0.82 | — | 0.38 | — |
| Silica (wt %) | — | 2.76 | 2.83 | — |
| Functional silane/silica | — | — | — | — |
| Methanol content ratio (ppm) | <1 | <1 | >1000 | <1 |
| Logarithmic rate of decrease (*Escherichia coli*) | — | — | — | — |
| Logarithmic rate of decrease (*Staphylococcus aereus*) | — | — | — | — |

(Cosmetic Evaluation/Measurement Methods)
<Hair Adhesion>
First, 3.0 g of the composite silicone rubber particle was added to 100 g of water and 3 g of ethanol and stirred, and the mixture was stirred for one minute at 1,000 rpm with a homo-disper to prepare a water-based cosmetic for hair treatment in the form of a water-based dispersion of the composite silicone rubber particle.

As hair for evaluation, a commercially available Chinese hair bundle (available from Beaulax, 17 cm, 2 g) was used after being bleached for 30 minutes at 50° C., and washed with a 10% Laureth sodium sulfate solution. After the hair bundle was immersed for 30 seconds in the water-based cosmetic for hair treatment, the hair bundle was rinsed with 1 L of water and dried. The amount of silicone adhering to the hair bundle was measured. In addition, the tactile sensation (moist feel and settling feel) after the treated hair was dried was evaluated. Cases in which all evaluation items were assessed as excellent were recorded as 5 points; cases assessed as inferior were recorded as 1 point; and intermediate cases were recorded as 2, 3, or 4 points. The average score was used as the evaluation result for the feel of use. The evaluation results are shown in Table 2.

Working Example 8

Water-Based Cosmetic (1):
First, 100 parts by weight of water, 3 parts by weight of ethanol, and 10.0 parts by weight of the composite silicone rubber particle of Working Example 7 were stirred for one minute at 1,000 rpm with a homo-disper to prepare a water-based cosmetic in the form of a water-based dispersion. After bleaching, a hair bundle that was washed with a 10% laureth sodium sulfate solution and dried was immersed in the cosmetic and then dried, and the hair adhesion, moisture, and settling feel of the hair bundle were evaluated. The results are shown in Table 2.

Working Example 9

Water-Based Cosmetic (2):
Performed in the same manner as in Working Example 8. However, the weight of the composite silicone rubber particle of Working Example 7 that were used was 3.0 parts by weight.

Working Example 10

Water-Based Composition (3):
Performed in the same manner as in Working Example 9. However, the particle obtained from Working Example 8 was used as the composite silicone rubber particle to be used, and the weight thereof was 3.0 parts by weight.

Comparative Example 5

Water-Based Cosmetic (4):
An attempt was made to prepare a water-based cosmetic for hair treatment in the form of a water-based dispersion in the same manner as in Working Example 9 with the exception of using 3.0 parts by weight of the composite silicone rubber particle of Comparative Example 2, but the composite silicone rubber particle separated and floated on the water surface, and a uniform solution was not obtained.

Comparative Example 6

Water-Based Cosmetic (5):
An attempt was made to prepare a water-based cosmetic for hair treatment in the form of a water-based dispersion in the same manner as in Working Example 9 with the exception of using 3 parts by weight of the silicone rubber particle of Comparative Example 4, but the composite silicone rubber particle separated and floated on the water surface, and a uniform solution was not obtained.

Working Examples 8 to 11 and Comparative Examples 5 and 6 are shown in Table 2.

TABLE 2

|  | Working Example 9 | Working Example 10 | Working Example 11 |
| --- | --- | --- | --- |
| Composite silicone rubber particle | (Particle obtained in Working Example 7) | (Particle obtained in Working Example 7) | (Particle obtained in Working Example 8) |
| Dispersibility | Water-based liquid dispersibility | Water-based liquid dispersibility | Water-based liquid dispersibility |
| Amount of hair adhesion (mass %) | 0.072 | 0.057 | 0.029 |
| Moisture | 4 | 4 | 4 |
| Settling feel | 4 | 4 | 4 |

|  | Comparative Example 5 | Comparative Example 6 |
| --- | --- | --- |
| Composite silicone rubber particle | (Particle obtained in Comparative Example 2) | (Particle obtained in Comparative Example 4) |
| Dispersibility | No dispersion (separated and floated on the water surface) | No dispersion (separated and floated on the water surface) |
| Amount of hair adhesion (mass %) | 0.013 | — |
| Moisture | 2 | — |
| Settling feel | 1 | — |

Formulation examples of the cosmetic of the present invention in which the cured silicone particle of the present invention can be compounded are described hereinafter. However, the present invention is not limited to these examples.

Formulation Example 1: W/O BB Cream (Components)
Phase A
1) Lauryl PEG/PPG-18/18 dimethicone (*1): 4 parts by mass
2) Caprylyl methicone (*2): 14 parts by mass
3) Ethylhexyl methoxycinnamate (*3): 7.5 parts by mass
4) Diethylamino hydroxybenzoyl hexyl benzoate (*4): 1.5 parts by mass
5) Ethylhexyl succinate: 2.5 parts by mass
6) Trimethylsiloxysilicic acid and polypropyl silsesquioxane (*5): 2 parts by mass
7) Composite silicone rubber particle of Working Examples 1 to 5: 3 parts by mass
8) Tocopherol acetate: 0.5 parts by mass
Phase B
9) Sodium ascorbyl sulfate: 0.5 parts by mass
10) Glycerin: 8 parts by mass
11) Sodium chloride: 0.7 parts by mass
12) Purified water: 39.8 parts by mass Phase C
13) Titanium oxide: 5.6 parts by mass
14) Yellow iron oxide (*6): 0.25 parts by mass
15) Red iron oxide (*7): 0.1 parts by mass
16) Black iron oxide (*8): 0.05 parts by mass
17) Phenyl trimethicone (*9): 9.2 parts by mass
18) Zinc oxide (*10): 0.8 parts by mass
*1: 5200 Formulation Aid, manufactured by Dow Corning Toray Co., Ltd.
*2: FZ-3196, manufactured by Dow Corning Toray Co.
*3: Uvinul MC80N, manufactured by BASF
*4: Uvinul A Plus Glanular, manufactured by BASF
*5: MQ-1640 Flake Resin, manufactured by Dow Corning Toray Co., Ltd.
*6: SA-TOY-8, manufactured by Miyoshi Kasei, Inc.
*7: SA-TOR-8, manufactured by Miyoshi Kasei, Inc.
*8: SA-TOB-8, manufactured by Miyoshi Kasei, Inc.
*9: SH556, manufactured by Dow Corning Toray Co., Ltd.
*10: Z-Cote, manufactured by BASF A BB cream of Formulation Example 1 is prepared in accordance with the following procedure.
1. Components 1 to 8 are mixed.
2. Components 9 to 12 are mixed.
3. Components 13 to 18 are mixed.
4. Phase A obtained in step 1 and phase C obtained in step 3 are mixed.
5. Phase B obtained in step 2 is gradually added and emulsified while stirring the mixture obtained in step 4.

Formulation Example 2: Nonaqueous Sunblock Lotion (Components)
Zinc oxide (*1): 6 parts by mass
Ethylhexyl methoxycinnamate (*2): 7.5 parts by mass
Dimethicone, dimethicone crosspolymer (*3): 24 parts by mass
Cyclopentasiloxane (*4): 60.5 parts by mass
Composite silicone rubber particle of Working Example 2: 2 parts by mass
*1: MZ-303S, manufactured by TAYCA
*2: Uvinul MC80N, manufactured by BASF
*3: 9041 Silicone Elastomer Blend, manufactured by Dow Corning Corporation
*4: SH245, manufactured by Dow Corning Toray Co., Ltd.

The nonaqueous sunblock lotion of Formulation Example 2 is prepared in accordance with the following procedure.
1. Components 4 and 5 are stirred until uniform.
2. The mixture of 1 above is added to component 3 and stirred until uniform.
3. Components 1 and 2 are mixed.
4. The mixtures of 2 and 3 above are stirred until uniform.

Formulation Example 3: O/W Anti-Aging Cream (Components)
Phase A
Purified water: balance
Methyl methacrylate crosspolymer (*1): 5 parts by mass
Phase B
Cyclopentasiloxane, cyclohexasiloxane (*2): 35 parts by mass
Silicone crosslinked product of the working examples: 5 parts by mass
(Hydroxyethyl acrylate/acryloyl dimethyl taurine Na) copolymer, squalane, polysorbate 80, water, and sorbitan oleate (*3): 0.7 parts by mass
(Hydroxyethyl acrylate/acryloyl dimethyl taurine Na) copolymer, isohexadecane, polysorbate 60, water, and sorbitan isostearate (*4): 0.7 parts by mass
Phase C
Dimethicone: 5 parts by mass
Dipalmitoyl hydroxyproline (*5): 0.5 parts by mass
Phase D
Wine extract (*6): 0.01 parts by mass
Fragrance: 0.2 parts by mass
Phase E
Phenoxy ethanol: 0.9 parts by mass
*1: Micropearl M305, manufactured by SEPPIC S.A.
*2: DC345, manufactured by Dow Corning Toray Co., Ltd.
*3: Simulgel EG, manufactured by SEPPIC S.A.
*4: Simulgel NS, manufactured by SEPPIC S.A.
*5: Simulgel DPHP, manufactured by SEPPIC S.A.
*6: Sepivinol R, manufactured by SEPPIC S.A.

The O/W anti-aging cream of Formulation Example 3 is prepared in accordance with the following procedure.
1. Component 2 is dispersed into component 1.
2. Component 4 is dispersed into component 3.
3. Components 5 and 6 are added to the mixture of 2 above and mixed. (Mixture 3)
4. Component 8 is dissolved in component 7. (Lysate 4)
5. Mixture 3, lysate 4, and Phase D described above are added and emulsified while stirring the mixture of 1 above.

Formulation Example 4: O/W Wrinkle Care Cream (Components)
Phase A
1) Cyclopentasiloxane (*1): 11 parts by mass
2) Composite silicone rubber particle of Working Example 6: 10 parts by mass
3) Lauryl PEG/PPG-18/18 dimethicone (*2): 0.5 parts by mass
4) PEG-12 dimethicone (*3): 4 parts by mass
Phase B
5) Purified water: 72.5 parts by mass
Phase C
Polyacrylamide, water, (C13, 14) isoparaffin, and Laureth-7 (*4): 2 parts by mass
*1: SH245, manufactured by Dow Corning Toray Co., Ltd.
*2: 5200 Formulation Aid, manufactured by Dow Corning Toray Co., Ltd.
*3: OFX-5329, manufactured by Dow Corning Toray Co., Ltd.
*4: Simulgel 305, manufactured by SEPPIC S.A.

The O/W wrinkle care cream of Formulation Example 4 is prepared in accordance with the following procedure.
1. Phase A is mixed until uniform.
2. The mixture of 1 above is gradually added while stirring phase B.
3. Phase C is added to the mixture of 2 above and mixed until uniform.

Formulation Example 5: Compact Foundation (Components)
Phase A
1) Cyclopentasiloxane, cyclohexasiloxane (*1): 4 parts by mass 2) Cetyl dimethicone (*2): 2 parts by mass
3) Stearyl dimethicone (*3): 6 parts by mass
4) Alkyl (C30-45) methicone, olefin (C30-45) (*4): 3 parts by mass
5) Beeswax (*5): 8 parts by mass
6) Cyclopentasiloxane, polypropyl silsesquioxane (*6): 5 parts by mass
7: Preservative: 0.5 parts by mass
Phase B
8) Cyclopentasiloxane (*7): 44 parts by mass
9) Red iron oxide (*8): 1.5 parts by mass
10) Yellow iron oxide (*9): 2.5 parts by mass
11) Black iron oxide (*10): 0.75 parts by mass
12) Brown iron oxide (*11): 5.75 parts by mass
Phase C
13) Silica (*12): 1 part by mass
14) Composite silicone rubber particle of Working Example 6: 6 parts by mass
15) Octenyl succinic acid corn starch Al (*13): 4 parts by mass
16) Talc: 2 parts by mass
17): Allantoin (*14): 1 part by mass
18) Titanium oxide: (*15): 3 parts by mass
*1: DC345, manufactured by Dow Corning Toray Co., Ltd.
*2: 2502 COSMETIC FLUID, manufactured by Dow Corning Toray Co., Ltd.
*3: 2503 COSMETIC FLUID, manufactured by Dow Corning Toray Co., Ltd.
*4: AMS-C30 COSMETIC FLUID, manufactured by Dow Corning Toray Co., Ltd.
*5: Cerabeil White No. 1, manufactured by Baerlocher France S.A.
*6: 670 FLUID, manufactured by Dow Corning Toray Co., Ltd.
*7: SH245, manufactured by Dow Corning Toray Co., Ltd.
*8: Unipure Red LC 381 AS-EM, manufactured by Sensient Cosmetic Technologies
*9: Unipure Yellow LC 182 AS-EM, manufactured by Sensient Cosmetic Technologies
*10: Unipure Black LC 989 AS-EM, manufactured by Sensient Cosmetic Technologies
*11: Unipure Brown LC 881, manufactured by Sensient Cosmetic Technologies
*12: LDP 1500, manufactured by Sensient Cosmetic Technologies
*13: Dry Flo Plus, manufactured by National Starch & Chemical Company
*14: Allantoin/ISP
*15: Matlake OPA-AS, manufactured by Sensient Cosmetic Technologies The compact foundation of Formulation Example 5 is prepared in accordance with the following procedure.
1. Phase A is heated to 80° C. and dissolved. (Lysate 1)
2. Components 9 to 12 are mixed until uniform. (Mixture 2)
3. Component 8 is dispersed into mixture 2. (Dispersion 3)
4. Phase C is mixed until uniform (Mixture 4)
5. Dispersion 3 and mixture 4 are mixed. (Mixture 5)
6. Mixture 5 is added while lysate 1 is stirred, and the mixture is stirred (80° C.).
7. The mixture is transferred to a container, cooled, and hardened.

Formulation Example 6: Hair Oil (Components)
1) Cyclopentasiloxane (*1): 45 parts by mass
2) Composite silicone rubber particle of Working Example 7: 2.7 parts by mass
3) Caprylyl methicone (*2): 20 parts by mass
4) Argan oil: 0.1 parts by mass
5) Olive oil: 0.1 parts by mass
6) Phenyl trimethicone (*3): 2 parts by mass
7) Cyclopentasiloxane, dimethiconol (*4): 30 parts by mass
8) Fragrance: 0.1 parts by mass
*1: SH245, manufactured by Dow Corning Toray Co., Ltd.
*2: SS-3408, manufactured by Dow Corning Toray Co., Ltd.
*3: 556 FLUID, manufactured by Dow Corning Toray Co., Ltd.
*4: PMX-1501 Fluid, manufactured by Dow Corning Toray Co., Ltd.

The hair oil of Formulation Example 7 is prepared in accordance with the following procedure.
1. Component 2 is dispersed into component 1. (Dispersion 1)
2. The remaining components 3 to 8 are added to dispersion 1 and mixed.

Formulation Example 7: Hair Spray

The numerical value after each component name indicates the parts by weight (mass).
Undiluted Solution
(Components)
1. Ethyl alcohol: balance
2. Acrylic resin alkanolamine solution (active ingredient: 50%): 7.0
3. Cetyl alcohol: 0.1
4. Composite silicone rubber particle of Working Example 7: 0.5
5. Fragrance: as appropriate
Filling
6. Undiluted solution: 50.0
7. Dimethyl ether: 50.0
(Manufacturing Procedure)
Step 1: Components 2 to 5 are added to component 1 and mixed and dissolved.
Step 2: The composition obtained in step 1 is filtered.
Step 3: A container (can) is filled with the composition (undiluted solution) obtained in step 2, and after a valve device is mounted, the container is filled with component 7.

Formulation Example 8: Conditioner

The numerical value after each component name indicates the parts by weight (mass).
(Components)
1. Stearyl trimonium chloride: 1.44
2. Cetyl alcohol: 2.4
3. Octyldodecanol: 0.5
4. Cetyl ethylhexanoate: 0.6
5. Squalane: 0.2
6. Purified water: balance
7. Glycerin: 2.0
8. Preservative: as appropriate
9. Fragrance: as appropriate 10. Composite silicone rubber particle of Working Example 3 (k): 3.0
11. Citric acid: as appropriate
*) O/W emulsion prepared by mixing the composite silicone rubber particle of Working Example 3 and dimethylpolysiloxane (2 cSt) at a 1/9 weight ratio and then emulsifying to a solid content of 30 mass %.

(Manufacturing Procedure)
Step 1: Components 1 to 5 are heated and mixed and dissolved.
Step 2: Components 6 to 7 are heated and mixed and dissolved.
Step 3: The composition obtained in step 2 is added to the composition obtained in step 1 and emulsified.
Step 4: The composition obtained in step 3 is cooled, and components 8 to 10 are added. Component 11 is also added as necessary.

After step 4, further adding dimethylsilicone, dimethylpolysiloxane capped at both molecular terminals with a dimethylsilanol group (dimethiconol), phenyl-modified silicone, amino-modified silicone, an emulsion such as amino polyether co-modified silicone, an aqueous dispersion of a silicone elastomer powder, and/or a water-soluble silicone oil such as a polyether-modified silicone makes it possible to anticipate a synergistic effect of each component.

Formulation Example 9: Hair Treatment Rinse Type

The numerical value after each component name indicates the parts by weight (mass).
(Components)
1. Cetyl alcohol: 5.6
2. Mineral oil: 1.0
3. Stearyl trimonium chloride: 1.2
4. Behentrimmonium chloride: 0.64
5. Cyclopentasiloxane: 2.0
6. Dimethicone (2 cSt): 1.0
7. Dimethicone (5,000 cSt): 1.0
8. Phenylmethicone: 2.0
9. Glycerin: 2.0
10. EDTA-2Na: 0.1
11. Purified water: balance
12. Panthenol: 0.1
13. Tocopherol: 0.04
14. Lysine HCl: 0.02
15. Glycine: 0.02
16. Histidine: 0.02
17. Composite silicone rubber particle of Working Example 3: 0.5
18. Preservative: as appropriate
19. Fragrance: as appropriate
(Manufacturing Procedure)
Step 1: Components 1 to 8 are heated and mixed and dissolved.
Step 2: Components 9 to 11 are heated and mixed and dissolved.
Step 3: The composition obtained in step 2 is added to the composition obtained in step 1 and emulsified.
Step 4: The composition obtained in step 3 is cooled, and components 12 to 19 are added.

In step 1, further adding dimethylpolysiloxane capped at both molecular terminals with a dimethylsilanol group (dimethiconol), amino-modified silicone, amino polyether co-modified silicone, and the like in addition to components 1 to 8 makes it possible to anticipate a synergistic effect of each component.

Formulation Example 10: Hair Treatment Rinse-on Type

The numerical value after each component name indicates the parts by weight (mass).
(Components)
1. Cetyl alcohol: 4.0
2. Mineral oil: 1.0
3. Stearyl trimonium chloride: 1.0
4. Behentrimonium chloride: 0.2
5. Cyclopentasiloxane: 1.2
6. Dimethicone (2 cSt): 0.6
7. Dimethicone (5,000 cSt): 0.6
8. Phenylmethicone: 1.2
9. Glycerin: 2.0
10. EDTA-2Na: 0.1
11. Purified water: balance
12: Panthenol: 0.1
13: Tocopherol: 0.04
14: Lysine HCl: 0.02
15: Glycine: 0.02
16: Histidine: 0.02
17. Composite silicone rubber particle of Working Example 3: 0.3
18. Preservative: as appropriate
19. Fragrance: as appropriate
(Manufacturing Procedure)
Step 1: Components 1 to 8 are heated and mixed and dissolved.
Step 2: Components 9 to 11 are heated and mixed and dissolved.
Step 3: The composition obtained in step 2 is added to the composition obtained in step 1 and emulsified.
Step 4: The composition obtained in step 3 is cooled, and components 12 to 19 are added.

In step 1, further adding dimethylpolysiloxane capped at both molecular terminals with a dimethylsilanol group (dimethiconol), amino-modified silicone, amino polyether co-modified silicone, and the like in addition to components 1 to 9 makes it possible to anticipate a synergistic effect of each component.

Formulation Example 11: Water-in-Oil Type Anti-Perspirant

Composition Wt. (%)
1. Silicone elastomer (*1) 7.0
2. Decamethyl cyclopentasiloxane: 10.0
3. Glyceryl trioctanoate: 7.0
4. Dipropylene glycol: 5.0
5. Sodium citrate: 0.2
6. Aluminum/zirconium tetrachlorohydrate: 18.0
7. Composite silicone rubber particle of Working Example 6: 7.0
8. Fragrance: as appropriate
9. Purified water: 45.8
Total: 100.0
*1: 9045 Silicone Elastomer Blend (manufacturing method), manufactured by Dow Corning Corporation
A: Components 1 to 3 were mixed.
B: Components 4 to 9 were mixed.
C: B was added to A and mixed and emulsified.

The water-in-oil type anti-perspirant obtained as described above demonstrated a light spread, no stickiness or oily feel, and no changes due to temperature or over time, and the usability and stability were also outstanding.

Formulation Example: Roll-on Type Anti-Perspirant

Composition Wt. (%)
1. Silicone elastomer (*1): 20.0
2. Dimethylpolysiloxane (6 mm2/s (25° C.)): 10.0
3. Dimethicone crosspolymer (*2): 15.0
4. Decamethyl cyclopentasiloxane: 30.0
5. Aluminum/zirconium tetrachlorohydrate: 20.0
6. Composite silicone rubber particle of Working Example 6: 5.0
7. Fragrance: as appropriate
Total: 100.0
*1: 9045 Silicone Elastomer Blend, manufactured by Dow Corning Corporation, was used.
*2: 9011 Silicone Elastomer Blend, manufactured by Dow Corning Corporation, was used.
(Manufacturing Method)
A: Components 1 to 4 were mixed.
B: Components 5 to 7 were added to A and dispersed uniformly.

The roll-on type anti-perspirant obtained as described above demonstrated a light spread, no stickiness or oily feel, and no changes due to temperature or over time, and the usability and stability were also outstanding.

Formulation Example: Skin Cream

TABLE 3

| Component | | Parts by weight |
|---|---|---|
| Oil phase | | |
| 1 | Lauryl PEG/PPG-18/18 dimethicone*1 | 2 |
| 2 | Bis(hydroxyethoxypropyl)dimethicone*2 | 2 |
| 3 | Isopropyl palmitate*3 | 1 |
| 4 | Cyclopentasiloxane*4 | 6.5 |
| 5 | Mineral oil*5 | 10 |
| 6 | Petrolatum | 1.5 |
| 7 | Composite silicone rubber particle (Working Example 3) | 5 |
| Aqueous phase | | |
| 8 | Glycerin | 5 |
| 9 | Sodium chloride | 1 |
| 10 | Water | 66 |

*1 5200 Formulation Aid, manufactured by Dow Corning Toray Co., Ltd.
*2 5562 Carbinol Fluid, manufactured by Dow Corning Toray Co., Ltd.
*3 Exceparl IPM, manufactured by Kao Chemicals
*4 SH245, manufactured by Dow Corning Toray Co., Ltd.
*5 Hicall K-230, manufactured by Kaneda Co., Ltd.

Formulation Example: Body Powder

TABLE 4

| Component | | Parts by weight |
|---|---|---|
| 1 | Titanium oxide | 13.43 |
| 2 | Yellow iron oxide*1 | 2.43 |
| 3 | Red iron oxide*2 | 0.97 |
| 4 | Black iron oxide*3 | 0.17 |

TABLE 4-continued

| Component | | Parts by weight |
|---|---|---|
| 5 | Composite silicone rubber particle (Working Example 3) | 51 |
| 6 | Fragrance | 2.5 |
| 7 | Cyclopentasiloxane*4 | 27.5 |
| 8 | (Ca/Na) borosilicate, titanium oxide*5 | 2 |

*1 SA-IOY-8, manufactured by Miyoshi Kasei, Inc.
*2 SA-IOR-8, manufactured by Miyoshi Kasei, Inc.
*3 SA-IOB-8, manufactured by Miyoshi Kasei, Inc.
*4 SH245, manufactured by Dow Corning Toray Co., Ltd.
*5 Pinpoints of Pearl, manufactured by BASF

INDUSTRIAL APPLICABILITY

The cured silicone particle of the present invention has excellent dispersibility in ethanol and silicone oil and is therefore easily compounded as an additive. In addition, when compounded as a cosmetic product composition into a cosmetic or an external preparation for skin, the tactile sensation thereof can be improved, so the silicone particle can be used as a skin cosmetic, a makeup cosmetic, an ointment, a hair cosmetic, or the like. Further, taking advantage of the physical properties thereof, the cured silicone particle of the present invention can also be used as an additive such as a thermosetting resin composition or a thermoplastic resin composition, or a surface lubricant for a plastic film.

The invention claimed is:

1. A composite silicone rubber particle, wherein a part or entire surface of the silicone rubber particle is covered by a fine particle, wherein a surface of the fine particle is modified by a compound that contains a quaternary ammonium salt, and wherein a methanol content in the composite silicone rubber particle is not greater than 10 ppm.

2. The composite silicone rubber particle according to claim 1, wherein the surface of the fine particle comprises at least one quaternary ammonium salt group represented by the following general formula (1):

$$(X^-R^1R^2{}_2N^+R^3-)_aY-$$

wherein $R^1$ is a hydrocarbon group having from 1 to 30 carbon atoms; each $R^2$ is independently a hydrogen atom or a hydrocarbon group having from 1 to 4 carbon atoms; each $R^3$ is independently selected from hydrocarbon groups having from 1 to 8 carbon atoms; X is a monovalent anionic group; a is an integer from 1 to 4; and Y is a divalent or higher valence linking group, which optionally contains a hetero-atom, bonded to the surface of the fine particle.

3. The composite silicone rubber particle according to claim 1, wherein at least one quaternary ammonium salt group is bonded to the surface of the fine particle via a silicon-containing linking group, and wherein a silicon atom in the linking group is bonded to the surface of the fine particle via an oxygen atom (—O—).

4. The composite silicone rubber particle according to claim 2, wherein a is 1 or 2.

5. The composite silicone rubber particle according to claim 1, wherein the compound comprises an N,N,N-octadecyldimethylammonium-chloride group or an N,N,N-trimethylammonium-chloride group.

6. The composite silicone rubber particle according to claim 1, wherein a content of quaternary ammonium salt groups is from 0.10 to 10 wt % of the entire composite silicone rubber particle.

7. The composite silicone rubber particle according to claim 1, wherein the surface of the fine particle comprises at least one silyl group represented by the following general formula (1'):

$$(X^-R^1R^2{}_2N^+R^3{-})_aY'{-}$$

wherein $R^1$ is a hydrocarbon group having from 1 to 30 carbon atoms; each $R^2$ is independently a hydrogen atom or a hydrocarbon group having from 1 to 4 carbon atoms; each $R^3$ is independently selected from hydrocarbon groups having from 1 to 8 carbon atoms; X is a monovalent anionic group; a is an integer from 1 to 4; and Y' is a linking group having a silicon atom bonded to an oxygen atom (—O—) on the surface of the fine particle; and wherein a weight ratio of the silyl group to fine particle is from 0.03 to 0.70.

8. The composite silicone rubber particle according to claim 1, wherein a content of the fine particle excluding a weight of the quaternary ammonium salt groups is from 0.5 to 10 wt % of the entire composite silicone rubber particle.

9. The composite silicone rubber particle according to claim 1, wherein the composite silicone rubber particle has antimicrobial activity.

10. The composite silicone rubber particle according to claim 1, wherein a methanol content in the composite silicone rubber particle is not greater than 1 ppm.

11. The composite silicone rubber particle according to claim 1, wherein the fine particle is silica or a resinified silicone particle or silsesquioxane or a silicone rubber particle having a smaller particle size than the silicone rubber particle.

12. A cosmetic product composition containing the composite silicone rubber particle according to claim 1.

13. A manufacturing method of a composite silicone rubber particle, said method comprising:
forming a composite silicone rubber particle by mixing a fine particle and a silicone rubber particle using a mechanical force;
modifying a surface of the fine particle of the composite silicone rubber particle with a silicon compound having a functional group containing quaternary ammonium salt and being capable of forming a chemical bond on the surface of the fine particle; and
reducing a methanol content of the composite silicone rubber particle to no greater than 10 ppm after the step of modifying.

14. A manufacturing method of a composite silicone rubber particle, said method comprising:
modifying surface of a fine particle with a silicon compound having a functional group containing quaternary ammonium salt and being capable of forming a chemical bond on the surface of the fine particle;
forming a composite silicone rubber particle by mixing the fine particle with a silicone rubber particle using a mechanical force; and
reducing a methanol content of the composite silicone rubber particle to no greater than 10 ppm after the step of modifying.

15. The manufacturing method of a composite silicone rubber particle according to claim 13, wherein the step of reducing is further defined as heating the fine particle at 65° C. or higher after the step of modifying, and wherein the methanol content of the composite silicone rubber particle is not greater than 1 ppm.

16. The manufacturing method of a composite silicone rubber particle according to claim 13, wherein the silicon compound is represented by the following general formula (2):

$$(Z^-R^4R^5{}_2N^+R^6{-})_b{-}R^7{-}SiR^8{}_3$$

wherein $R^4$ is a hydrocarbon group having from 1 to 30 carbon atoms; each $R^5$ is independently a hydrogen atom or a hydrocarbon group having from 1 to 4 carbon atoms; each $R^6$ is independently a hydrocarbon group having from 1 to 8 carbon atoms; $R^7$ is a divalent or higher valence organic linking group or a hetero-atom; each $R^8$ is independently an alkoxy group, a hydroxyl group, an alkyl group, or an alkylene group, with the proviso that at least one $R^8$ is an alkoxy group; Z is a monovalent anionic group; and b is an integer from 1 to 4.

17. The manufacturing method of a composite silicone rubber particle according to claim 13, wherein the fine particle has a hydroxyl group on the surface thereof.

18. The manufacturing method of a composite silicone rubber particle according to claim 14, wherein the step of reducing is further defined as heating the fine particle at 65° C. or higher after the step of modifying, and wherein the methanol content of the composite silicone rubber particle is not greater than 1 ppm.

19. The manufacturing method of a composite silicone rubber particle according to claim 14, wherein the silicon compound is represented by the following general formula (2):

$$(Z^-R^4R^5{}_2N^+R^6{-})_bY'{-}R^7{-}SiR^8{}_3$$

wherein $R^4$ is a hydrocarbon group having from 1 to 30 carbon atoms; each $R^5$ is independently a hydrogen atom or a hydrocarbon group having from 1 to 4 carbon atoms; each $R^6$ is independently a hydrocarbon group having from 1 to 8 carbon atoms; $R^7$ is a divalent or higher valence organic linking group or a hetero-atom; each $R^8$ is independently an alkoxy group, a hydroxyl group, an alkyl group, or an alkylene group, with the proviso that at least one $R^8$ is an alkoxy group; Z is a monovalent anionic group; and b is an integer from 1 to 4.

20. The manufacturing method of a composite silicone rubber particle according to claim 14, wherein the fine particle has a hydroxyl group on the surface thereof.

* * * * *